US011137382B2

(12) United States Patent
Brauer et al.

(10) Patent No.: US 11,137,382 B2
(45) Date of Patent: Oct. 5, 2021

(54) APPARATUS AND METHOD FOR PERFORMING GAS ANALYSIS USING OPTICAL ABSORPTION SPECTROSCOPY, SUCH AS INFRARED (IR) AND/OR UV, AND USE THEREOF IN APPARATUS AND METHOD FOR PERFORMING DISSOLVED GAS ANALYSIS (DGA) ON A PIECE OF ELECTRICAL EQUIPMENT

(71) Applicant: MORGAN SCHAFFER LTD., LaSalle (CA)

(72) Inventors: Stephan Brauer, Montreal (CA); Stefan Voinea, Brossard (CA)

(73) Assignee: MORGAN SCHAFFER LTD., LaSalle (CA)

( * ) Notice: Subject to any disclaimer, the term of this patent is extended or adjusted under 35 U.S.C. 154(b) by 78 days.

(21) Appl. No.: 16/434,650

(22) Filed: Jun. 7, 2019

(65) Prior Publication Data
US 2019/0383731 A1 Dec. 19, 2019

Related U.S. Application Data

(60) Provisional application No. 62/685,497, filed on Jun. 15, 2018.

(51) Int. Cl.
*G01N 33/28* (2006.01)
*G01N 21/3504* (2014.01)
*G01J 3/42* (2006.01)

(52) U.S. Cl.
CPC ............ *G01N 33/2841* (2013.01); *G01J 3/42* (2013.01); *G01N 21/3504* (2013.01)

(58) Field of Classification Search
CPC .... G01N 21/25; G01N 21/251; G01N 21/255; G01N 21/27; G01N 21/272; G01N 21/29;
(Continued)

(56) References Cited

U.S. PATENT DOCUMENTS 2,806,144 A * 9/1957 Berger ............... G01N 21/3504
250/346
4,112,737 A * 9/1978 Morgan ................... G01N 7/10
73/19.02
(Continued)

FOREIGN PATENT DOCUMENTS

WO WO 2018/126273 7/2018
WO WO 2018/231196 12/2018

OTHER PUBLICATIONS

Tang et al. "On-Line Analysis of Oil-Dissolved Gas in Power Transformers Using Fourier Transform Infrared Spectrometry," Energies, Nov. 2018, vol. 11, 3192, 15 pages.
(Continued)

*Primary Examiner* — Gordon J Stock, Jr.
(74) *Attorney, Agent, or Firm* — Sheridan Ross P.C.

(57) ABSTRACT

An apparatus and associated a method are described for performing gas analysis on a gas sample. The method comprising exciting the gas sample with one or more electromagnetic energy sources and obtaining optical absorption signals associated with the gas sample prior to application of a catalytic process to the gas sample as well as during and/or after application of the catalytic process to the gas sample. The obtained optical absorption signals may then be processed using differential calculation approaches to derive information associated with the gas sample, which may include for example information conveying concentrations of certain specific gases in the gas sample. In some implementations, the optical absorption measurement system is configured to use the one or more electromagnetic energy sources to excite the gas sample to produce first optical absorption signals. The optical absorption measurement system is also configured to apply a catalytic process to the gas sample to derive a modified gas sample and to use the one or more electromagnetic energy sources to excite the (Continued)

modified gas sample to produce second optical absorption signals. Information may then be derived at least in part by processing the first optical absorption signals and second optical absorption signals. The apparatus and associated method may find practical uses in a variety of fields including, without being limited to, the field of dissolved gas analysis (DGA) for detecting/monitoring faults in liquid-insulated electrical equipment as well as equipment used for mine safety, particularly coal mines; equipment for analyzing gases that emerge from the bore hole during drilling for natural gas and oil and equipment for identifying gas leaks in underground natural gas lines as well as other areas.

56 Claims, 12 Drawing Sheets

(58) Field of Classification Search
CPC ............ G01N 21/31; G01N 21/3103; G01N 21/3504; G01N 21/3554; G01N 21/3577; G01N 21/3581; G01N 21/359; G01N 2021/354; G01N 2021/3545; G01N 33/2847; G01N 2021/3125; G01N 2021/3129; G01N 2021/3155; G01N 2021/3159; G01N 2021/3166; G01N 2021/317; G01N 33/2841; G01J 3/0235; G01J 3/42

See application file for complete search history.

(56) References Cited

U.S. PATENT DOCUMENTS

| | | | |
|---|---|---|---|
| 4,444,040 A * | 4/1984 | Sakai | G01N 33/2841 73/19.02 |
| 4,582,950 A | 4/1986 | Busse et al. | |
| 4,803,052 A * | 2/1989 | Abromaitis | G01N 21/75 422/91 |
| 6,037,592 A * | 3/2000 | Sunshine | G01N 21/3504 250/343 |
| 6,391,096 B1 | 5/2002 | Waters et al. | |
| 6,526,805 B1 | 3/2003 | Babed-Dornea et al. | |
| 6,906,630 B2 | 6/2005 | Georges et al. | |
| 7,239,977 B2 | 7/2007 | Fantana et al. | |
| 7,255,836 B2 * | 8/2007 | Lehmann | G01N 33/0013 29/592 |
| 7,263,871 B2 | 9/2007 | Selker et al. | |
| 7,398,672 B2 | 7/2008 | Riddle | |
| 7,765,871 B2 | 8/2010 | Riddle | |
| 8,347,687 B2 | 1/2013 | Cunningham et al. | |
| 8,484,150 B2 | 7/2013 | Sparling et al. | |
| 8,616,045 B2 * | 12/2013 | Cavallini | G01N 33/2841 73/19.11 |
| 8,738,301 B2 | 5/2014 | Frotscher et al. | |
| 8,743,365 B2 * | 6/2014 | Dong | G01N 21/33 356/437 |
| 9,176,107 B2 | 11/2015 | Jeffrey et al. | |
| 9,182,342 B2 * | 11/2015 | Engstrand | G01N 21/41 |
| 9,194,797 B2 | 11/2015 | Liu et al. | |
| 9,234,834 B2 | 1/2016 | Van Mechelen et al. | |
| 9,377,451 B2 * | 6/2016 | Panella | G01N 21/783 |
| 9,500,580 B1 * | 11/2016 | Mitra | G01N 33/004 |
| 9,666,351 B2 | 5/2017 | Larsson | |
| 9,739,706 B2 | 8/2017 | Maity et al. | |
| 9,759,610 B2 * | 9/2017 | Maity | G01N 25/4873 |
| 9,869,634 B2 | 1/2018 | Palanganda Poonacha et al. | |
| 9,880,142 B2 | 1/2018 | Potyrailo et al. | |
| 9,884,269 B2 | 2/2018 | Hunter et al. | |
| 10,001,518 B2 | 6/2018 | Cheim et al. | |
| 10,024,836 B2 | 7/2018 | Robinson | |
| 10,132,789 B2 | 11/2018 | Hollunder et al. | |
| 10,302,618 B2 * | 5/2019 | Kuriyama | G01N 30/02 |
| 10,365,209 B1 * | 7/2019 | Beaudoin | G01N 33/26 |
| 10,429,371 B2 * | 10/2019 | Virtanen | B01F 3/04503 |
| 10,495,623 B2 * | 12/2019 | Hinshaw | G01N 33/2841 |
| 10,832,854 B2 * | 11/2020 | Buijs | H01F 27/402 |
| 2009/0192340 A1 * | 7/2009 | Culp | C07C 5/333 585/440 |
| 2011/0154806 A1 * | 6/2011 | Hoyte | G01J 3/10 60/276 |
| 2013/0045541 A1 * | 2/2013 | Fix | G01N 21/3504 436/164 |
| 2013/0098462 A1 * | 4/2013 | Hoskin | F17D 3/00 137/3 |
| 2014/0025211 A1 | 1/2014 | Cheim et al. | |
| 2014/0165704 A1 * | 6/2014 | Maity | G01N 33/2841 73/25.01 |
| 2015/0355080 A1 * | 12/2015 | Mitchell | G01N 21/3504 356/73 |
| 2017/0212093 A1 | 7/2017 | Virtanen et al. | |
| 2018/0209319 A1 * | 7/2018 | Bradford | C07B 33/00 |
| 2018/0259444 A1 | 9/2018 | Buijs et al. | |
| 2018/0259451 A1 | 9/2018 | Buijs et al. | |
| 2018/0321138 A1 * | 11/2018 | Li | G01N 21/8507 |
| 2021/0102889 A1 * | 4/2021 | Brauer | G01N 21/255 |

OTHER PUBLICATIONS

Zhu et al. "A One ppm NDIR Methane Gas Sensor with Single Frequency Filter Denoising Algorithm," Sensors, Sep. 2012, vol. 12, No. 9, pp. 12729-12740.

* cited by examiner

APPARATUS AND METHOD FOR PERFORMING GAS ANALYSIS USING OPTICAL ABSORPTION SPECTROSCOPY, SUCH AS INFRARED (IR) AND/OR UV, AND USE THEREOF IN APPARATUS AND METHOD FOR PERFORMING DISSOLVED GAS ANALYSIS (DGA) ON A PIECE OF ELECTRICAL EQUIPMENT

CROSS-REFERENCE TO RELATED APPLICATIONS

For the purposes of the United States, this application claims the benefit of priority under 35 USC § 119(e) based on U.S. Provisional Patent Application Ser. No. 62/685,497, which was filed on Jun. 15, 2018 and which is presently. The contents of the above-noted application are incorporated herein by reference.

TECHNICAL FIELD

This disclosure generally relates to the field of gas analysis apparatuses using optical absorption spectroscopy (such as for example infrared (IR) or ultra-violet (UV) spectroscopy) and, more specifically, gas analysis apparatuses for measuring concentrations (including trace quantities) of specific gases in a gas sample. The approach described in the present document may be applied to a wide variety of gas measurement methodologies, including but without being limited to Dispersive IR, Non-dispersive IR, Photoacoustic Spectroscopy, Fourier Transform IR, Gas correlation spectroscopy and Tunable Diode Laser Spectroscopy. This disclosure may find practical uses in a variety of fields including the field of dissolved gas analysis (DGA) for detecting/monitoring faults in liquid-insulated electrical equipment; the field of mine safety, particularly coal mines, where gas concentrations can reach levels that are dangerous for breathing or potentially explosive; the field of gas exploration for analysing gases that emerge from the bore hole during drilling for natural gas and oil, in order to guide the drilling toward gas reserves (mud logging); identifying gas leaks in underground natural gas lines as well as other areas.

BACKGROUND

There are various devices commercially available that use optics-based methods, such as infrared light (IR) and/or ultra-violet (UV) light, to detect and to obtain gas concentration measurements from a sample gas. These monitors vary significantly by their design and even by their basic operating principles depending on the manufacturer.

Typically optical gas analysis devices, such as IR-based as well as UV-based gas analysis devices, rely on the principle that when molecules in a gas sample are exposed to light, they absorb light as they shift into an excited molecular state, as illustrated in FIG. 1. For each type of gas component, the absorbed wavelengths are different and form gas specific "fingerprints", which can be used to identify specific gas components and to quantify the concentration of such gas components in the gas sample. FIG. 2 is a schematic illustration of such a typical optical gas analysis device. As depicted, a typical optical gas analysis device 260 would include a light source 262, one or more band-pass filters 263, a gas cell 264 (for holding a gas sample to be analysed), a mirror 266, and detectors 268. By using the one or more band-pass filters 263 to select specific wavelengths and then measuring the light received at the detectors 268, it is possible to derive measurements conveying concentrations of some specific types of gases. Note that some gas molecules like $O_2$, $N_2$, $H_2$ do not absorb light on mid IR-range wavelengths meaning that other sensing technology and/or a different wavelength range would be needed to measure those gases.

While the principles of operation of optical gas analysis devices, such as IR-based as well as UV-based gas analysis devices, are known, challenges arise when applying these principles in certain practical implementations in particular in implementations in which it is desirable to obtain gas concentration measurements for trace quantities of certain specific gases. In particular, conventional systems are typically unsuitable for measuring a quantity of a specific gas when the quantity of the specific gas present in a gas sample is very small relative to the gas sample and these conventional systems are neither sufficiently sensitive nor sufficiently selective to be able to discern trace quantities of specific gases.

One specific practical area in which it is desirable to obtain gas concentration measurements for trace quantities of specific gases in a gas sample is in the field of dissolved gas analysis (DGA) for detecting/monitoring faults in liquid-insulated electrical equipment. Electrical insulating liquid (such as for example mineral oil) is commonly used in equipment that serves in the generating, transmitting, and distributing of electrical power. Such equipment generally includes transformers (sometimes called oil-immersed transformers), tap-changers and circuit breakers. In such equipment, the liquid acts both as an electrical insulating medium and a vehicle for heat dissipation. When a fault occurs in such electrical equipment, fault gases may evolve in the insulating liquid.

Some of the gases that are typically associated with specific fault types in such equipment are Hydrogen ($H_2$), Carbon Dioxide ($CO_2$), Carbon Monoxide (CO), Ethane ($C_2H_6$), Methane ($CH_4$), Ethylene ($C_2H_4$) and Acetylene ($C_2H_2$). Analysis of one or more of such fault gases may be used to provide a diagnosis of the health of electrical equipment.

In this regard, various practical Dissolved Gas Analysis (DGA) applications have been previously suggested for detecting such fault gases in equipment that serves in the generating, transmitting and distributing of electrical power.

For example, U.S. Pat. No. 6,391,096 to Waters describes an apparatus for performing dissolved gas analysis on electrical insulating oil which makes use of a gas chromatograph to analyze the fault gases. The contents of the aforementioned document are incorporated herein by reference. The apparatus includes a tubular membrane extractor column for extracting the fault gases from the oil, where the column includes a plurality of composite hollow fiber tubes coated with a thin layer of a non-porous gas permeable polymer, making each tube gas permeable, but not dielectric fluid permeable. Diffusion of the fault gases occur through the fiber tubes until equilibrium exists on both sides of the phase barrier. The time required to reach equilibrium or near equilibrium conditions depends upon factors such as pressure and temperature, the size of the diffusing molecules and the permeation properties of the media, as well as the flow rate of the oil carrying the gases for equilibrium.

U.S. Pat. No. 8,347,687 to Cunningham describes an apparatus for performing dissolved gas analysis on electrical insulating oil which makes use of photo-acoustic spectroscopy (PAS) to analyze the fault gases. The contents of the aforementioned document are incorporated herein by reference. The apparatus includes a gas extraction module in which the fault gases are released from the oil by means of an agitator into a head space of the module. After a period of agitation, head space equilibrium is achieved, and the gases are pumped into an analysis cell where measurements of the head space gases are performed with a PAS module. The apparatus conveniently includes a fluid conduit configuration which enables the measure of oil samples from different sources relatively easily while minimizing or avoiding cross contamination.

A deficiency associated with many commonly used apparatuses performing dissolved gas analysis on electrical insulating liquid (such as for example electrical insulating oil) using infra-red absorption methods is that they frequently require relatively large sample gas volumes to be able to detect the minimal concentrations of fault gases that are relevant for detecting emerging faults in liquid-insulated electrical equipment. For example, such minimal concentrations may represent gas levels as low as 1 ppm in the case of acetylene. The requirement for relatively large sample gas volumes, however, increases manufacturing costs of other systems in the apparatus, including those required to maintain the liquid/gas samples within a specific operational temperature range to ensure measurement accuracy and reproducibility. In addition, the relatively large sample gas volumes required often lead to increases in the period of time required to extract the fault gases from each sample (i.e., the time required to reach equilibrium), which negatively impacts the time-resolution and accuracy of dissolved-gas concentration measurements of many conventional DGA apparatuses.

Another challenge associated with the use of IR absorption methods to obtain dissolved-gas concentration measurements for trace quantities of DGA gases is that the sample gas frequently contains amounts of gases other than the targeted DGA gases as well as vapours, including water vapour, and the presence of such compounds in the sample gas may interfere with optical spectroscopy-based methods designed to quantify the concentrations of the DGA gases.

Against the background described above, it is clear that there remains a need in the industry to provide improved optical spectroscopy-based gas analysis apparatuses and methods for measuring concentrations (including trace quantities) of certain specific gases in a gas sample that alleviate at least some of the deficiencies of the existing apparatuses and methods.

SUMMARY

This Summary is provided to introduce a selection of concepts in a simplified form that are further described below in the Detailed Description. This Summary is not intended to identify key aspects or essential aspects of the claimed subject matter.

In accordance with a first aspect, a method for performing gas analysis on a gas sample is provided, the method comprising: exciting the gas sample with one or more electromagnetic energy sources and obtaining optical absorption signals associated with the gas sample: (i) prior to application of a catalytic process to the gas sample; and (ii) during and/or after application of the catalytic process to the gas sample; processing the obtained optical absorption signals to derive information associated with the gas sample.

Conceptually, the application of a catalytic process to the gas sample may change the concentration of certain specific gas species in the gas sample, which may affect the optical absorbency characteristics of the gas sample. Advantageously, by measuring the optical absorption from a gas sample before and after (and/or during) application of a catalytic process, the optical absorption contributions of specific gas species reactive to the catalytic process applied can be better distinguished from that of the other gases present in gas sample, which may enhance the sensitivity and/or selectivity of concentration measurements of the specific gas species.

The approach may be applied to a wide variety of optical gas measurement methodologies, including, without being limited to, Dispersive IR, Non-dispersive IR, Photoacoustic Spectroscopy, Fourier Transform IR, Gas correlation spectroscopy and Tunable Diode Laser Spectroscopy.

In specific practical implementations, various specific types of catalytic processes may be used and the selection of one or more specific catalytic processes may be made in dependence of the specific target gas species for which information (such as for example concentration) is to be derived. Examples of catalytic processes that may be contemplated include, without being limited to a combustion process and a hydrogenation process. In addition, in some practical implementations, multiple catalytic processes may be applied to the gas sample, either in parallel or in series, in order to modify the chemical nature/properties of certain specific gas species in the gas sample and obtained additional optical measurements.

In accordance with some specific implementations, the derived information associated with the gas sample may convey concentrations of one or more specific target gases in the gas sample. The specific target gases will depend on properties of the one or more electromagnetic energy sources, including possible band filters used in conjunction therewith, as well as on the nature of the catalytic process being applied. In some specific implementations, the one or more specific target gases may be selected from the set consisting of carbon dioxide ($CO_2$), carbon monoxide (CO), ethane ($C_2H_6$), methane ($CH_4$), ethylene ($C_2H_4$) and acetylene ($C_2H_2$).

In accordance with some specific implementations, processing the obtained optical absorption signals to derive information comprises: deriving concentrations of different component species in the gas sample; and assessing the derived concentrations of the different component species to derive diagnostic information.

In specific practical implementations, various specific types of electromagnetic energy sources may be used including, without being limited to an IR electromagnetic energy source and an UV electromagnetic energy source.

In accordance with another aspect, an apparatus for performing dissolved gas analysis on a piece of electrical equipment having components immersed in electrical insulating liquid is provided. The apparatus comprises:
  a. a gas extraction system configured for extracting gas from the electrical insulating liquid;
  b. an analyser in fluid communication with the gas extraction system for performing gas analysis on the extracted gas, the analyser including an optical absorption measurement system configured to excite the extracted gas with one or more electromagnetic energy sources and to obtain optical absorption signals associated with the extracted gas:
    i. prior to application of a catalytic process to the extracted gas; and
    ii. during and/or after application of the catalytic process to the extracted gas;
  c. a processing system programmed for deriving information associated with dissolved gas concentrations in the electrical insulating liquid at least in part by processing the optical absorption signals obtained by the analyser.

In some specific practical implementations, the apparatus may comprise a liquid inlet and a liquid outlet connectable to the piece of electrical equipment for allowing electrical insulating liquid to circulate between the piece of electrical equipment and the apparatus through a liquid circulation path, the gas extraction system being in communication with the liquid circulation path. The apparatus may in some cases include a pump for circulating the electrical insulating liquid through the liquid circulation path. It is to be appreciated that other configurations allowing the electrical insulating liquid to be provided to the gas extraction system are possible and will become apparent to the person skilled in the art of dissolved gas analysis on a piece of electrical equipment. The apparatus may be configured to be used with a variety of different pieces of electrical equipment including, without being limited to, a transformer, a tap-changer and a circuit breaker.

In specific practical implementations, various specific types of electromagnetic energy sources may be used in the apparatus including, without being limited to an IR electromagnetic energy source and an LT electromagnetic energy source.

In some specific implementations, the optical absorption measurement system includes an optical pathway for propagating the electromagnetic energy from the one or more electromagnetic energy sources, at least part of the extracted gas lying in the optical pathway. The optical absorption signals produced by the analyser may include first optical absorption signals and second optical absorption signals. The absorption measurement system may be configured to:
  i. use the one or more electromagnetic energy sources to excite the extracted gas to produce the first optical absorption signals;
  ii. apply the catalytic process to the extracted gas to derive a modified extracted gas; and
  iii. use the one or more electromagnetic energy sources to excite the modified extracted gas to produce the second optical absorption signals.

In some specific practical implementations, the one or more electromagnetic energy sources may be used to excite the modified extracted gas to produce the second optical absorption signals:
  a. after completion or interruption of the application of the catalytic process to the extracted gas; and/or
  b. during the application of the catalytic process to the extracted gas.

In some specific practical implementations, the derived information may convey concentrations of one or more specific target gases in the extracted gas. The processing system may in some implementations be programmed for assessing the derived concentrations of the different component species to derive diagnostic information pertaining to piece of electrical equipment. In non-limiting examples, the diagnostic information may convey excesses (and/or insufficiencies) in concentrations of certain specific target gases, increasing/decreasing trends in concentrations and/or gas ratios and/or other information that may be useful in connection with the specific target gases.

In some specific practical implementations, the optical absorption measurement system includes a catalytic reactor configured to apply the catalytic process to the extracted gas. Various specific types of catalytic processes may be used and specific catalytic processes may be selected in dependence of the specific target gas species for which information is to be derived. Examples of catalytic processes that may be contemplated include, without being limited to a combustion process and a hydrogenation process. In addition, in some practical implementation, multiple catalytic processes may be applied to the gas sample, either in parallel or in series, in order to react specific gas species in the gas sample and obtain additional optical measurements.

In some specific practical implementations, the catalytic process may include a combustion process configured to combust at least some combustible gases in the extracted gas in a process that consumes $O_2$ and to form combustion by-products including at least one of $H_2O$ and $CO_2$. The catalytic reactor applying the catalytic process may include a catalytic element, such as for example a catalytic surface or other suitable catalytic element, for applying the catalytic process. In some implementations, the catalytic reactor may be configured for heating the catalytic element to initiate or accelerate the catalytic process being applied to the extracted gas.

In some specific practical implementations, the catalytic process may include a hydrogenation process configured to consume $H_2$ in the extracted gas and to transform at least some hydrocarbon gases in the extracted gas into other hydrocarbon gases of higher molecular weight.

It is to be appreciated that while a combustion process and a hydrogenation process have been specifically set forth as examples of catalytic processes that may be considered, it is to be appreciated that other catalytic processes may also be considered in the context of other implementations and that such other processes may become apparent to the person skilled in the art in view of the present description.

In some specific practical implementations, the optical absorption measurement system may be configured for adjusting temperature and/or pressure characteristics of the extracted gas so that the optical absorption signals are obtained at similar temperatures and pressures. More specifically, in some implementations, the optical absorption measurement system may include a pressure regulating system for controlling pressure characteristics of at least one of the extracted gas and the modified extracted gas so that the pressure characteristics of the extracted gas when the first optical absorption signals are produced are similar to the pressure characteristics of the modified extracted gas when the second optical absorption signals are produced. In some implementations, the pressure regulating system may configured to introduce an external gas to a volume holding the extracted gas and/or the modified extracted gas to obtain a mixed-gas, wherein the obtained mixed-gas has a pressure approaching a target pressure. Different types of external gases may be used in practical implementations including, without being limited to, ambient air, dry air and nitrogen (Na. The optical absorption measurement system may instead/also include a temperature regulating system for controlling temperature characteristics of at least one of the extracted gas and the modified extracted gas so that the temperature characteristics of the extracted gas when the first optical absorption signals are produced are similar to the temperature characteristics of the modified extracted gas when the second optical absorption signals are produced.

In some specific practical implementations, the optical absorption measurement system may include one or more additional optical pathways for propagating electromagnetic energy from the one or more electromagnetic energy sources in order to obtain other measurements, which may allow normalizing the measurements to account for imperfections and/or drift of optical components of the apparatus. More specifically, in some implementations, the optical pathway of the optical absorption measurement system is first optical pathway and the optical absorption measurement system includes a second optical pathway for propagating electromagnetic energy from the one or more electromagnetic energy sources, a reference gas lying in the second optical pathway. The optical absorption measurement system may be configured to use the one or more electromagnetic energy sources to excite the reference gas lying in the second optical pathway when producing the optical absorption signals. The first optical pathway and the second optical pathway may be configured to direct electromagnetic energy to a same detector and may converge subsequent to the first optical pathway traversing the extracted gas and the second optical pathway traversing the reference gas.

In some specific practical implementations, the gas extraction system may include a semi-permeable membrane for extracting gas from the electrical insulating oil. The quantity gas the gas extraction system may be configured for extracting from the electrical insulating liquid may vary. In a non-limiting example, the extracted gas has a volume of less than 10 cubic centimeters (10 cc) and preferable between 3 cc and 10 cc.

In some specific practical implementations, the information associated with the dissolved gas concentrations in the insulating liquid derived by the processing system may convey concentrations of one or more specific gases, such as for example but without being limited to, gases selected from the group consisting of carbon dioxide ($CO_2$), carbon monoxide (CO), ethane ($C_2H_6$), methane ($CH_4$), ethylene ($C_2H_4$) and acetylene ($C_2H_2$).

In some specific practical implementations, the optical absorption measurement system may include a plurality of optical filters for filtering the electromagnetic energy from the one or more electromagnetic energy sources, the optical filters in the plurality of optical filters being associated with respective frequency bands corresponding to specific target gases. In a non-limiting implementation, the optical absorption measurement system may include an optical wheel assembly including at least some of the plurality of optical filters. Alternatively, the optical absorption measurement system may include one or more tunable optical interferometer assemblies for filtering the electromagnetic energy from the one or more electromagnetic energy sources.

In specific practical implementations, different types of electromagnetic energy sources include may be used in the optical absorption measurement system including, but without being limited to, a light emitting diode (LED), a laser, a hot filament, micromachined (MEMS) IR emitter, a halogen lamp and any combination of a light emitting diode (LED), a laser, a hot filament, micromachined (MEMS) IR emitter and a halogen lamp.

In some specific practical implementations, the apparatus may be configured for establishing a communication link over a computer network with a remote computing device for transmitting the derived information associated with dissolved gas concentrations in the electrical insulating liquid. The remote device may be any suitable computing device, such as for example a tablet, smartphone and personal computer.

In accordance with another aspect, a method for performing dissolved gas analysis on a piece of electrical equipment having components immersed in electrical insulating liquid is provided. The method comprises:

a. causing electrical insulating liquid to be directed to a gas extraction system;

b. using the gas extraction system to extract gas from the electrical insulating liquid;

c. using an analyzer including an optical absorption measurement system to perform gas analysis on the extracted gas, wherein using the analyzer to perform gas analysis comprises exciting the extracted gas with one or more electromagnetic energy sources and obtaining optical absorption signals associated with the gas sample:

1. prior to application of a catalytic process to the gas sample; and 2. during and/or after application of the catalytic process to the gas sample;

d. processing the obtained optical absorption signals to derive information associated with dissolved gas concentrations in the electrical insulating liquid.

In some specific practical implementations, the step of using the gas extraction system to extract the gas from the electrical insulating liquid includes waiting a certain period of time to allow gas from the electrical insulating liquid to accumulate in a head space of a cell in the gas extraction system.

In some specific practical implementations, the optical absorption signals include first optical absorption signals and second optical absorption signals, wherein using the analyzer to perform gas analysis comprises: (i) using the one or more electromagnetic energy sources to excite the extracted gas to produce the first optical absorption signals; (ii) applying the catalytic process to the extracted gas to derive a modified extracted gas; and (iii) using the one or more electromagnetic energy sources to excite the modified extracted gas to produce the second optical absorption signals.

In specific practical implementations, various specific types of catalytic processes may be used and specific catalytic processes may be selected in dependence of the specific target gas species for which information is to be derived. Examples of catalytic processes that may be contemplated include, without being limited to, a combustion process and a hydrogenation process. In some implementations, applying the catalytic process may include heating a catalytic element to initiate or accelerate the catalytic process.

In some specific practical implementations, the one or more electromagnetic energy sources may be used to excite the modified extracted gas to produce the second optical absorption signals: (i) after completion or interruption of the application of the catalytic process to the extracted gas; and/or (ii) during the application of the catalytic process to the extracted gas.

In specific practical implementations, the method may comprise adjusting temperature and/or pressure characteristics of the extracted gas so that the optical absorption signals are obtained at similar temperatures and pressures. For example, the method may comprising using a pressure (or temperature) regulating system for controlling pressure (temperature) characteristics of the extracted gas and/or the modified extracted gas so that the pressure (temperature) characteristics of the extracted gas when the first optical absorption signals are produced are similar to the pressure (temperature) characteristics of the modified extracted gas when the second optical absorption signals are produced.

In some specific practical implementations, the method may further comprise using the one or more electromagnetic energy sources to excite a reference gas to produce reference optical absorption signals and processing the reference optical absorption signals and the optical absorption signals obtained by exciting the extracted gas to derive the information associated with dissolved gas concentrations in the electrical insulating liquid.

In accordance with another aspect, an apparatus for performing gas analysis on a gas sample. The apparatus comprises an analyser including an optical absorption measurement system configured to excite the gas sample with one or more electromagnetic energy sources and to obtain optical absorption signals associated with the gas sample: (i) prior to application of a catalytic process to the gas sample; and (ii) during and/or after application of the catalytic process to the gas sample. The apparatus also comprises a processing system in communication with the analyser for receiving the optical absorption signals, the processing system being configured for processing the obtained optical absorption signals to derive information associated with the gas sample.

It is to be understood that the equipment that serves in the generating, transmitting, and distributing of electrical power, as referred to in the present description, refers to transformers (sometimes called oil-immersed transformers), tap-changers and circuit breakers, and/or any other electrical asset for which detecting/measuring a gas dissolved in insulating liquid may be used as an indication of fault detection/diagnosis of the equipment.

In the present description, it is also to be understood that the term "gas" can refer to a plurality of gases and/or may embrace the term "vapour".

All features of exemplary embodiments which are described in this disclosure and are not mutually exclusive can be combined with one another. Elements of one embodiment or aspect can be utilized in the other embodiments/aspects without further mention. Other aspects and features of the present invention will become apparent to those ordinarily skilled in the art upon review of the following description of specific embodiments in conjunction with the accompanying Figures.

BRIEF DESCRIPTION OF THE DRAWINGS

A detailed description of specific exemplary embodiments is provided herein below with reference to the accompanying drawings in which.

Figure 1:
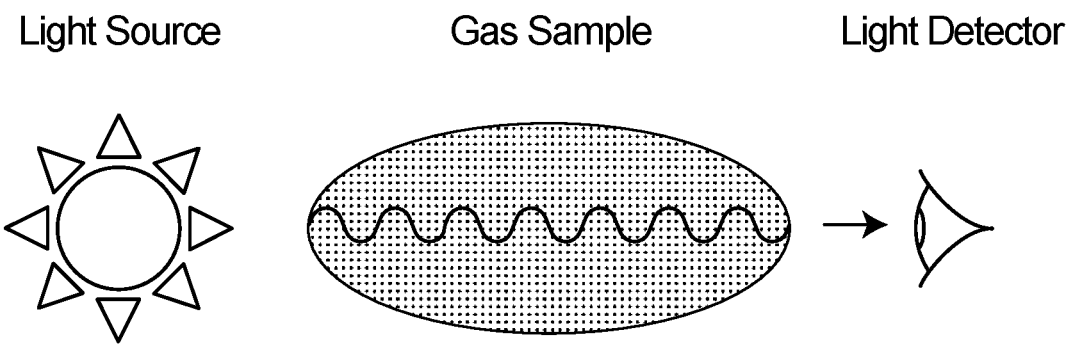
FIG. 1 is a schematic illustration of basic principles of a light detector configured to detect light absorption by a gas sample.
Figure 2:
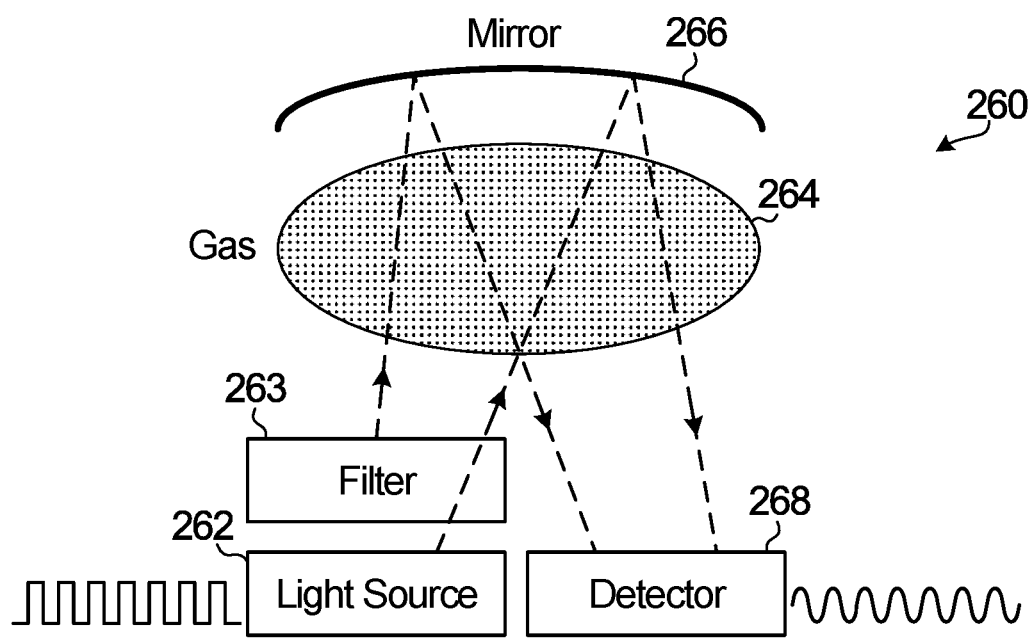
FIG. 2 is a schematic illustration of a basic optical module in accordance with known principles.

In the drawings, exemplary embodiments are illustrated by way of example. It is to be expressly understood that the description and drawings are only for the purpose of illustrating certain embodiments and are an aid for understanding. They are not intended to be a definition of the limits of the invention.

DETAILED DESCRIPTION OF EMBODIMENTS

A detailed description of one or more specific embodiments of the invention is provided below along with accompanying Figures that illustrate principles of the invention. The invention is described in connection with such embodiments, but the invention is not limited to any specific embodiment. The scope of the invention is limited only by the claims. Numerous specific details are set forth in the following description in order to provide a thorough understanding of the invention. These details are provided for the purpose of describing non-limiting examples and the invention may be practiced according to the claims without some or all of these specific details. For the purpose of clarity, technical material that is known in the technical fields related to the invention has not been described in great detail so that the invention is not unnecessarily obscured.

The approach described in the present document may be applied to a wide variety of optical gas measurement methodologies, including but without being limited to IR-based gas measurement methodologies (Gas Infrared Absorption Spectroscopy (GIRAS)) such as Dispersive IR, Non-dispersive IR, Photoacoustic Spectroscopy, Fourier Transform IR, Gas correlation spectroscopy and Tunable Diode Laser Spectroscopy.

The approaches described may also be applied to methodologies using other portions of the optical spectrum such as for example, but without being limited to, the ultra-violet (UV) spectrum. For the purpose of conciseness and simplicity, the specific embodiments presented will focus of the use of a source of radiation operating in the infra-red range of the spectrum. It is to be appreciated that other sources operating in a different range of the spectrum (such as the UV range) may also be used and that such other sources may in some cases be more optimally suited for certain specific target gases to be measured due to their specific associated absorbency spectrum.

Figure 3:
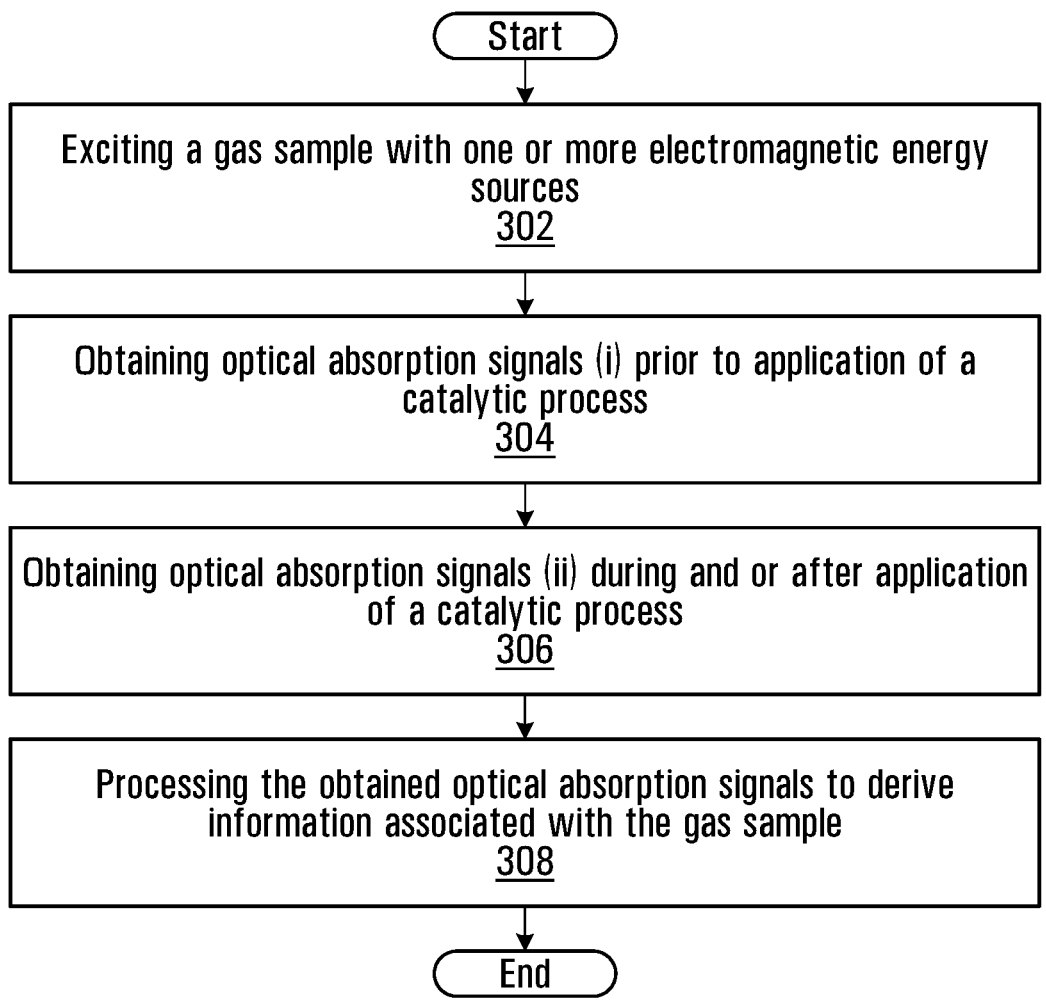
FIG. 3 is a flow diagram of a process for performing gas analysis on a gas sample in accordance with an example of implementation of the present invention.

FIG. 3 is a flow diagram of a process for performing gas analysis on a gas sample in accordance with an example of implementation of the present invention;

As shown, at step 302 a gas sample is excited with one or more electromagnetic energy sources. At step 304, optical absorption signals associated with the gas sample are obtained prior to application of a catalytic process to the gas sample. At step 306, optical absorption signals associated with the gas sample are obtained during and/or after application of the catalytic process to the gas sample. At step 308, the obtained optical absorption signals are processed to derive information associated with the gas sample.

The derived information associated with the gas sample may convey concentrations of one or more specific target gases in the gas sample. Optionally, the derived concentrations of the different component species may be processed to derive diagnostic information, examples of which will be presented later on with reference to specific practical implementations.

Advantageously, by measuring the optical absorption properties of a gas sample before and after (and/or during) application of a catalytic process, the optical absorption contributions of specific gas species reactive to the catalytic process applied can be better distinguished from the other gases present in gas sample, which may enhance the sensitivity and/or selectivity of concentration measurements of the specific gas species.

The approach described aims to improve sensitivity and accuracy of GIRLS schemes and other optical measurement devices by taking advantage of "differential" measurements, whereby two or more absorption measurements are used, in combination with signal processing methods, to compensate for different artifacts in the system including offset and gain drifts as well as overlaps in absorption spectrum of certain gas species. The use of differential measurement methods has been used in GIRAS systems and typically such methods seek to keep constant as many of the measurement conditions as possible between the two or more absorption measurements. In the approach described, the "differential" measurements are taken by measuring optical absorption properties of a gas sample before and after (and/or during) application of a catalytic process and processing these measurements using a model description of the IR absorption apparatus and a model description of the combustion processes.

As will be described in greater detail below with reference to specific practical embodiments, various specific types of catalytic processes may be used and the selection of one or more specific catalytic processes may be made in dependence of the specific target gas species for which information (such as for example concentration) is to be derived. Examples of catalytic processes that may be contemplated include, without being limited to a combustion process and a hydrogenation process. In addition, in some practical implementation, multiple catalytic processes may be applied to the gas sample, either in parallel or in series, in order to modify the chemical nature/properties of certain specific gas species in the gas sample and obtained additional optical measurements.

In the description below, a very specific practical implementation of the present invention will be presented in the context of dissolved gas analysis (DGA) applications using optical absorption measurements, and in particular Infrared (IR) absorption spectroscopy measurements, for detecting/ measuring concentrations of one or more specific gases that may be dissolved in electrical insulating liquid of that type that may be used for example in transformers, tap-changers and circuit breakers. It is to be appreciated that the concepts presented in the present document having regard to gas analysis using optical absorption spectroscopy measurements may be used in other practical applications in which it is desirable to measure small quantities of gas in a gas sample. Such other practical applications may include for example, without being limited to the field of mine safety, particularly coal mines, where gas concentrations can reach levels that are dangerous for breathing or potentially explosive; the field of gas exploration for analysing gases that emerge from the bore hole during drilling for natural gas and oil, in order to guide the drilling toward gas reserves (mud logging); identifying gas leaks in underground natural gas lines as well as other fields of applications that may become apparent to the person skilled in the art in view of the present description.

Infrared (IR) absorption spectroscopy includes illuminating a gas sample contained in a closed gas-filled volume or cell with electromagnetic radiations and measuring the resultant absorption signal using a detector. It is well understood in the art that each gas species has an individual infrared (IR) absorption spectrum and the level of absorption is generally directly proportional to the gas concentration in a given volume.

One practical application includes detecting/diagnosing faults in electrical equipment that serves in the generation, transmission and/or distribution of electrical power for example, but not limited to, a transformer, a tap-changer or a circuit breaker, having components immersed in electrical insulating liquid, such as electrical insulating oil. In such practical implementations, dissolved gas analysis can provide timely insight into the condition of the electrical equipment by identifying and quantifying fault gases which are dissolved in the insulating liquid of the electrical equipment. Moreover, such dissolved gas analysis can assist in early detection of electrical equipment faults, minimizing costly unplanned outages and equipment failure. Examples of electrical equipment faults, such as power transformers faults, can include arcing, partial discharge and overheating (pyrolysis).

Dissolved Gas Analysis Apparatus

Figure 4:
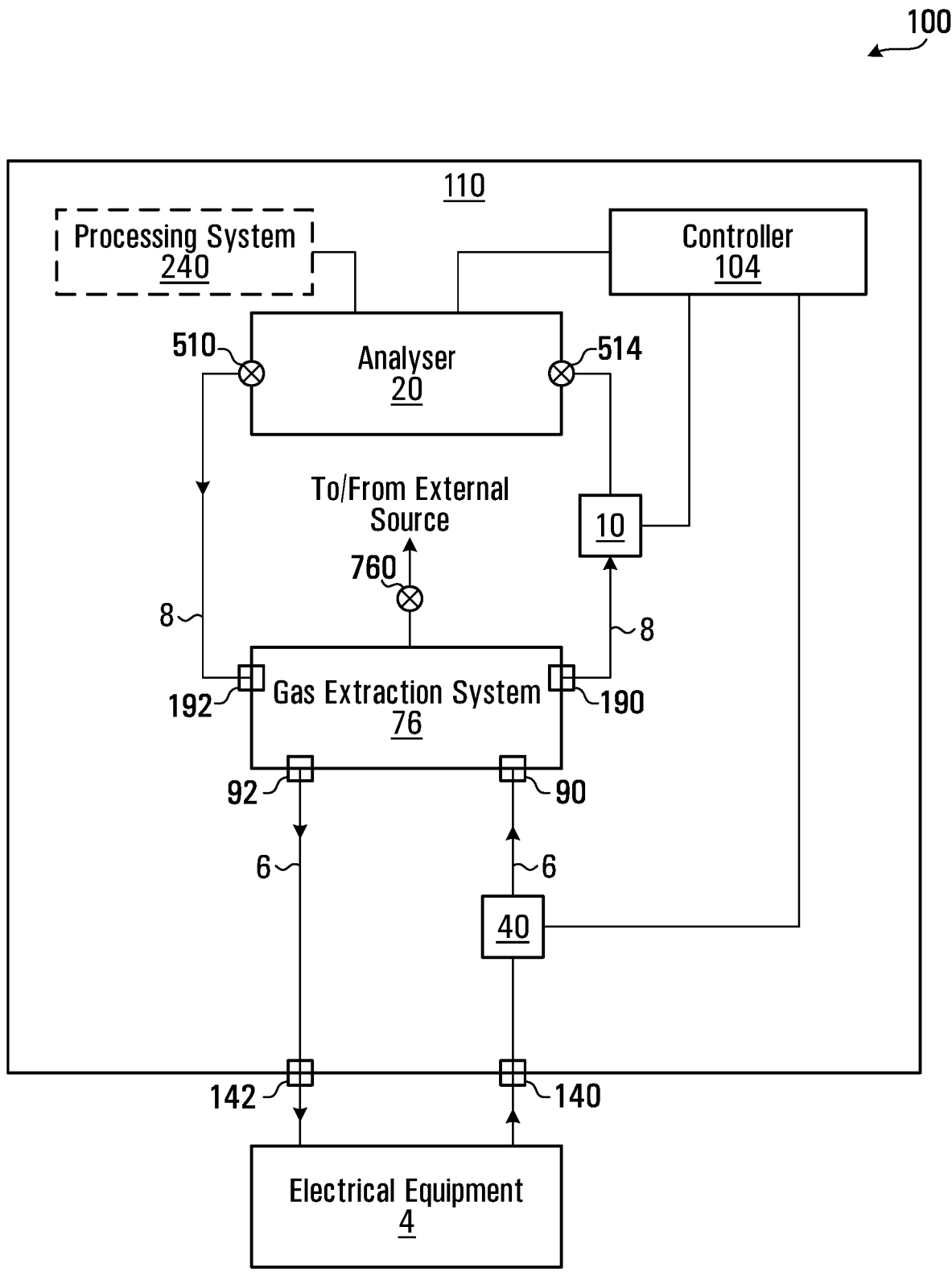
FIG. 4 is a functional block diagram of a dissolved gas analysis (DGA) apparatus 100 connected to a piece of electrical equipment 4, wherein the DGA apparatus 100 includes an analyser 20 in fluid communication with a gas extraction system 76, a controller 104 and a processing system 240, in accordance with a non-limiting example of implementation of the present invention.

A specific example of implementation of a dissolved gas analysis apparatus 100 is shown in the block diagram of FIG. 4.

In this example, the apparatus 100 includes a housing 110 which encloses various elements for performing dissolved gas analysis on a piece of electrical equipment 4 having components immersed in electrical insulating liquid, such as electrical insulating oil for example. The housing 110 can be made of any suitable material including but not limited to plastic, metal or a composite.

In a specific practical implementation, the apparatus 100 can be configured to be portable and be embodied in a housing 110 of a compact size dimensions and weight such that the apparatus 100 can be used as a portable apparatus connectable to a piece of electrical equipment 4 containing electrical insulating liquid when a DGA operation is desired. In another specific practical implementation, the apparatus 100 is configured to be a fixed/stationary device, which is connected to the piece of electrical equipment 4 containing electrical insulating liquid and can be left connected to the piece of electrical equipment 4 for an extended length of time. In such cases the housing 110 of the apparatus may be configured to be securely mountable upon a supporting surface, such as a wall or frame, for example by providing suitable mounting elements and/or suitable fasteners on the housing 110 to facilitate such mounting.

In the specific example depicted, the apparatus 100 includes a liquid inlet 140 and a liquid outlet 142 connectable to the piece of electrical equipment 4 for allowing electrical insulating liquid to circulate between the piece of electrical equipment 4 and the apparatus 100 over a liquid circulation path 6, which transfers insulating liquid in and out of the apparatus 100.

The apparatus 100 further includes a gas extraction system 76 in communication with the liquid circulation path 6. The gas extraction system 76 is configured for extracting gas from the electrical insulating liquid. In some specific practical implementations, the gas extraction system 76 may be configured for holding a sample of the electrical insulating liquid from the piece of electrical equipment 4 in order to extract gas from that oil sample or, alternatively, the gas extraction system 76 may be configured for extracting gas as the electrical insulating liquid travels through the liquid circulation path 6. It is to be appreciated that the insulating liquid traveling through the liquid circulation path 6 may include dissolved gases and gas bubbles. A more detailed description of a specific practical implementation of the gas extraction system 76 and its operation is provided later in this text.

The apparatus 100 also includes an analyser 20 in fluid communication with the gas extraction system 76 over fluid circulation path 8 for performing gas analysis on the extracted gas from the electrical insulating liquid by the gas extraction system 76. The fluid circulation path 8 allows fluid travel from the extraction system 76 to the analyser 20 as well as from the analyser 20 to the extraction system 76. In other words, in the specific example depicted, the fluid circulation path 8 creates a closed loop configuration between the analyser 20 and the gas extraction system 76 for the sample gas to travel through. An advantage of a closed loop configuration is that it may accelerate the speed at which equilibration of gas concentrations between the extraction system 76 and the gas analyser 20 is reached. A more detailed description of the analyser 20 and its operation is provided later in this text. While the examples depicted and described in the present description show closed loop configurations, it is to be appreciated by the person skilled in the art that, in alternate implementations (not shown), e.g., a single connecting conduit between the gas extraction system 76 and the analyser 20 may instead be used.

The apparatus 100 further includes one or more suitable pumps 10 for causing and controlling a flow of gas along the fluid circulation path 8, in and out of the analyser 20. While a specific location for one pump 10 along the fluid circulation path 8 is shown in FIG. 4, it will be apparent to the person of skill that other locations and/or more than one pump 10 may be present depending on specific implementations.

The apparatus 100 further includes a suitable pump 40 for controlling a flow of liquid in the liquid circulation path 6 from the piece of electrical equipment 4 to the apparatus 100 and through the gas extraction system 76. It will be apparent to the person of skill that other locations for the pump 40 may be suitable for this purpose.

The apparatus 100 further includes a controller 104 for controlling the operations of the different features/components of the apparatus 100. In specific practical implementations, the controller 104 includes suitable hardware and/or software for controlling the operational settings of the different features of the apparatus 100, including the pumps 40 and 10 and valves (not shown) for controlling the flow of insulating liquid and extracted gas (through liquid circulation path 6 and fluid circulation path 8) and the operations of analyser 20. In some specific practical implementations, the controller 104 may receive electrical power from an electric power source that is connected to the controller 104 via service wiring (not shown). The controller 104 may be configured in different suitable manners, which will become apparent to the person skilled in the art in view of the present description and thus will not be described in further detail here.

In addition, the apparatus 100 may further include a processing system 240 programmed for processing signals generated by the analyser 20 to derive, amongst other, information conveying concentrations of specific gas species present in the insulating liquid and/or to derive information conveying a fault status (or alternatively a fault level ranking) of the electrical equipment 4.

It is to be appreciated that while the gas extraction system 76 has been depicted and described with reference to FIG. 4 as lying outside the piece of electrical equipment 4, in certain alternative embodiments (not depicted in the Figures) the gas extraction system 76 may be configured differently and may be positioned in a space within the piece of electrical equipment 4. In certain implementations still (not depicted in the Figures), the liquid circulation path 6 and/or the circulation pump 40, may be omitted and the apparatus 100 may instead rely on other fluid circulation mechanisms for circulating the electrical insulating liquid through the gas extraction system 76. Such alternative physical configurations, as well as others, for providing suitable gas extraction functionality are known and/or will become apparent to the person skilled in the art of DGA in view of the present description and will therefore not be described in further detail here.

The following sections of this text will describe in greater detail various features of the apparatus 100 and the manner in which they may interact with one another in specific implementations.

Analyser 20

In the example depicted, the analyser 20 is in fluid communication with the gas extraction system 76 over fluid circulation path 8 for performing gas analysis on the gas extracted from the electrical insulating liquid by the gas extraction system 76 to produce an optical absorption signal associated with the extracted gas. In specific practical implementations the analyser 20 is configured for producing a signal conveying concentration information of one of more of the following fault gases: carbon dioxide ($CO_2$), carbon monoxide (CO), ethane ($C_2H_6$), methane ($CH_4$), ethylene ($C_2H_4$) and acetylene ($C_2H_2$).

The analyser 20 includes a number of elements for performing the gas analysis on the gas extracted from the electrical insulating liquid.

For example, the analyser 20 includes an optical absorption measurement system, which in this specific embodiment is embodied as an IR absorption measurement system 200 (e.g., shown in FIG. 5), which is configured to contain and excite the gas extracted from the electrical insulating liquid by the gas extraction system 76. Upon exciting the extracted gas, the IR absorption measurement system 200 is also further configured for generating signals which conveys information associated with the extracted gas. A more detailed description of the IR absorption measurement system 200 and its operation is provided later in this text.

The analyser 20 may be in communication with the processing system 240, which may include one or more processing units programmed for processing the IR absorption signals generated by the IR absorption measurement system 200 conveying information associated with the extracted gas to derive information associated with the extracted gas, which may convey concentrations of specific gas species present in the insulating liquid and/or to derive diagnostic information, which may convey a fault status (or alternatively a fault level ranking) of the electrical equipment 4. In a specific implementation, the fault status may convey the presence (or absence) of a detected fault associated with the electrical insulating liquid in the electrical equipment 4, such as for example an excess concentration in one or more of certain specific fault gases. In some specific implementations, a fault level ranking may be derived and instead of the fault status or in combination therewith to convey on a graded scale a level of criticality in connection with the derived excess concentrations of certain specific fault gases. The specific scale used may vary from one implementation to the other and is not critical to the present invention and thus will not be described in further detail here.

In some specific practical implementations, the processing system 240 may be configured for comparing a derived concentration of a specific target fault gas in the insulating liquid to a reference range of concentrations for that fault gas in order to identify potential deviations from expected measurements and detect potential on-going or developing faults in the electrical equipment 4. It is to be appreciated that a detected potential on-going or developing fault in the electrical equipment 4 may be expressed in absolute terms (for example a fault is or is not present) or alternatively as a gradated fault level ranking conveying how far from an expected concentration range the measurement of the specific target Fault gas is. Alternatively, or in addition, the processing system 240 may be configured for processing a derived concentration of a specific target fault gas in the insulating liquid to (i) detect excesses (and/or insufficiencies) in concentrations (e.g. by comparing the concentration to a reference range of concentrations); (ii) to detect increasing/decreasing trends in concentrations of the specific target fault gas and/or (iii) to detect excesses (and/or insufficiencies) in ratios of gases and/or (iv) to perform other useful assessments on the derived concentration of the specific target fault gas to derive other information that may be useful in connection with the specific fault gases.

The processing system 240 may be further programmed for generating signals for causing the information conveying the fault status (or alternatively a fault level ranking) of the electrical equipment 4 and/or the derived information conveying concentration of specific gas species present in the insulating liquid to be displayed on a display device. The display device may be comprised of any suitable visual elements including a display screen, a series of lighting elements (e.g. light-emitting diodes (LEDs)) or any other suitable element that may suitably convey the information to a human operator. In some embodiments, the display device may be part of the apparatus 100 or, alternatively, the display device may reside in a computing device (not shown in the figures) located remotely from the apparatus 100 wherein the computing device is in communication with the apparatus 100 over a data communication link.

It will be apparent to the reader that, in some embodiments, the processing system 240 functionality may be embodied, in whole or in part, on a processing assembly including suitable hardware and/or software components physically located within the apparatus 100. In such embodiment, the processing system 240 may be in communication with the analyser 20 (over circuit wiring for example) for receiving optical absorption signals generated by the measurement system 200 of the analyser 20 which conveys information associated with the gas sample to derive information conveying concentrations of specific gas species present in the insulating liquid and/or to derive information conveying a fault status (or alternatively a fault level ranking) of the electrical equipment 4. The processing system 240 may also be connected to a display device (not shown) part of the apparatus 100 and may be programmed for causing the display of the information conveying the fault status (or alternatively a fault level ranking) of the electrical equipment 4 and/or the derived information conveying concentration of specific gas species present in the insulting liquid.

In an alternative implementation, the processing system 240 may instead be embodied, in whole or in part, on a processing assembly including suitable hardware and/or software components physically located remotely from the apparatus 100. In such embodiment, the processing system 240 may be located in a remote computing device in communication with to the apparatus 100 over a short-range wireless connection or over a private or public (Internet) computer network. In such cases, it will become apparent to the person of skill in the art that the apparatus 100 would be equipped with suitable network interface hardware and software for establishing communications with the remote computing device.

In yet another alternative implementation, the processing system 240 functionality may be performed in whole or in part "in the cloud" (not shown) to derive information conveying concentrations of specific gas species present in the insulting liquid and/or to derive information conveying a fault status (or alternatively a fault level ranking) of the electrical equipment 4.

Cloud computing has, amongst other, the advantage of allowing the specific processes (including the software) used to derive useful information to be modified and/or upgrades as well as new functionality to be introduced in one centralized location and thus without requiring access to the individual physical apparatus 100. For entities making use of a large number of apparatuses 100, this may result in significant time savings and associated cost savings.

A more detailed description of the processing system 240 and the functionality that it may provide in some implementations is provided later in this text.

Optical Absorption Measurement System 200

Figure 5:
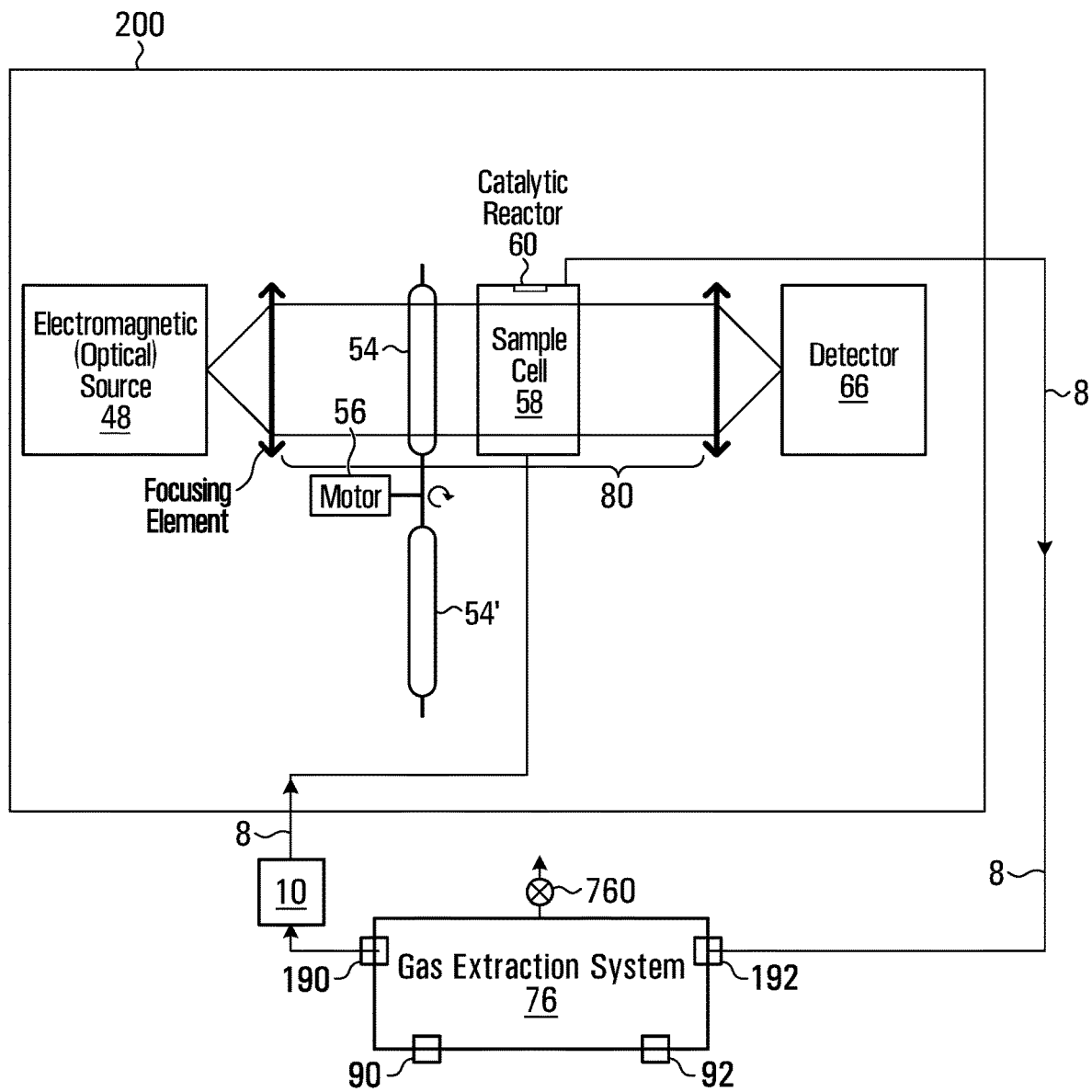
FIG. 5 shows a more detailed block diagram of an optical absorption measurement system 200 for use in connection with the analyser 20 of the DGA apparatus 100 of FIG. 4 in accordance with a first specific non-limiting example of implementation of the present invention.
Figure 6:
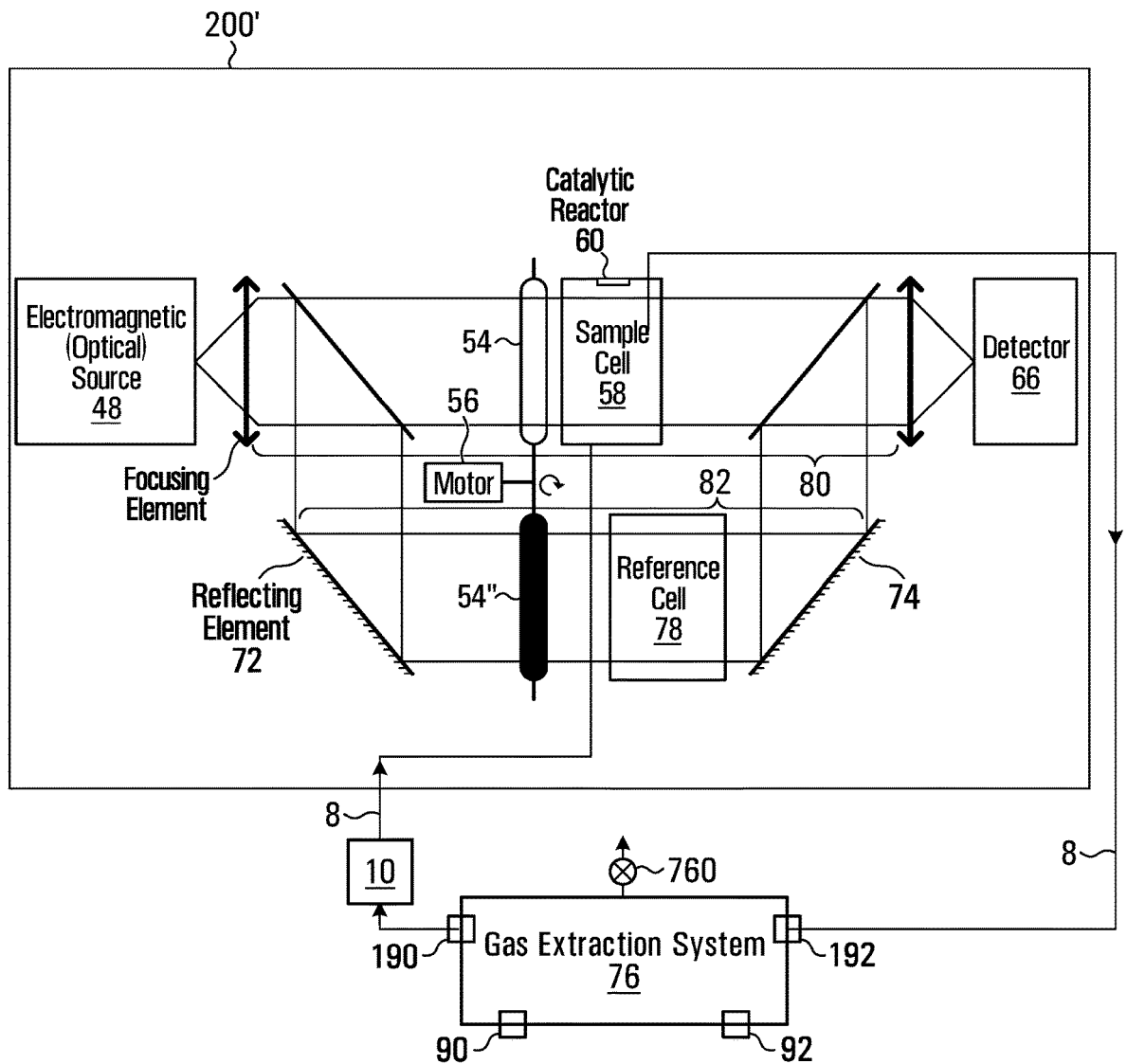
FIG. 6 shows a more detailed block diagram of an optical absorption measurement system for use in connection with the analyser 20 of the DGA apparatus 100 of FIG. 4 in accordance with a second specific non-limiting example of implementation of the present invention.

FIG. 5 shows a conceptual block diagram of a first practical non-limiting implementation of an optical absorption measurement system 200 that may be used in the analyser 20, which is in fluid communication with the gas extraction system 76 over fluid circulation path 8. FIG. 6 shows a block diagram of a second practical implementation of an optical absorption measurement system 200' of the analyser 20, which is in fluid communication with the gas extraction system 76 over fluid circulation path 8. For the purpose of simplicity, elements of optical absorption measurement system 200 and optical absorption measurement system 200' that are common to one another are being designated with same reference numerals in both figures.

FIG. 5 shows a very specific configuration for an optical absorption measurement system 200 with one electromagnetic energy source 48, one detector 66 and one optical pathway 80 traversing a gas sample volume in the form of a sample cell 58 containing the gas to be analyzed. The detector 66 is configured for obtaining measurements of electromagnetic energy propagated from the electromagnetic energy source 48 through the gas the sample cell 58. The detector 66 has a sensing input for obtaining measurements of electromagnetic energy propagated through the gas the sample cell 58, and an output for generating optical absorption signals indicative of optical absorption measurements which are representative of a concentration of a specific target gas being detected. In practical implementations, detectors 66 may be embodied in, for example, without being limited to, photo-acoustic, photodetector, thermocouple, thermopile, Golay cell, pyroelectric and combinations of these.

The sample cell 58 is connected to fluid circulation path 8 for circulating gas extracted from the electrical insulating liquid by the gas extraction system 76. Suitable interconnections, including suitable channels and valves (not shown) may be provided for controlling the flow of gas through the sample cell 58. It should be noted that while in the depicted example, the gas sample volume has been shown to be in the form of a sample cell 58 other types of gas sample volumes different shapes may also be contemplated. As an example of an alternate gas sample volume, the reader is invited to refer to international patent publication No. WO2016/179693 published Nov. 17, 2016, which describes a photoacoustic detector having resonant cavities (gas sample volumes) of different shapes including a cavity having a curved shape and a cavity having varying cross-sectional dimensions along its length. The contents of the aforementioned document are incorporated herein by reference.

In the configuration of FIG. 5, a motor 56 is provided to turn a wheel allowing different optical filters 54 54' to be introduced in the optical pathway 80 to thereby selectively excite optical absorption of different gas species of the gas in the sample cell 58. In communication with the sample cell 58 is a catalytic reactor 60 for applying a catalytic process to the gas in the gas sample cell 58. By controlling the catalytic reactor 60 to apply a catalytic process optical absorption measurements can be made before and after (and/or during) application of the catalytic process to the gas.

FIG. 6 shows another very specific configuration for an optical absorption measurement system 200', analogous to optical absorption measurement system 200 with one electromagnetic energy source 48, one detector 66, a first optical pathway 80 traversing a gas sample cell 58 containing the gas to be analyzed and a second optical pathway 82 traversing a reference cell 78 containing a known/reference gas. As was the case with reference to the configuration of FIG. 5, a motor 56 is provided to turn a wheel allowing different optical filters 54 to be introduced in the optical pathway 80 to thereby selectively excite optical absorption of different gas species of the gas in the sample cell 58. In this configuration, the optical filters are arranged on the wheel in such a manner that only one of optical pathways 80 and 82 is illuminated at a time by the electromagnetic energy source 48, the other optical pathway being blocked by an opaque portion of the wheel. In the embodiment depicted in FIG. 6, the optical filter 54' of FIG. 5 was replaced with an opaque element 54" to block the optical pathway 82. As a result, the optical absorption signals generated by detector 66 can be associated with one of the two optical pathways 80 and 82. In communication with the sample cell 58 is a catalytic reactor 60 for applying a catalytic process to the gas in the gas sample cell 58. By controlling the catalytic reactor 60 to apply a catalytic process optical absorption measurements can be made before and after (and/or during) application of the catalytic process to the gas. Optical absorption measurements obtained through the second optical pathway 82 traversing a reference cell 78 allow compensation of system gain and imperfections over time, including gain contributions and/or drift from the electromagnetic energy source 48, contamination (e.g. dirt build-up) of the optical elements including filter elements 54, reflecting elements 72 and 74, the detector 66, air paths through the first and second optical pathways 80 82 and electronics.

It is to be appreciated that while in the configuration depicted in FIGS. 5 and 6 the catalytic reactor 60 has been depicted and being located inside (or as being part) of the sample cell 58, other suitable configurations may be contemplated. For example, in an alternate configuration, the catalytic reactor may be located in a gas volume distinct from the sample cell 58 and be connected thereto through a suitable set of conduits, valves and pumps to facilitate gas flow between the sample cell 58 and the gas volume in which the catalytic reactor applies the catalytic process. In addition, while a single catalytic reactor 60 has been depicted, it is to be appreciated that alternative implementations may include two, three or more catalytic reactors configured to apply respective catalytic processes either sequentially or in parallel depending upon the type of information that it is desirable to obtain. Alternate suitable configurations will become apparent to the person skilled in the art in view of the present descriptions.

Figure 7A:
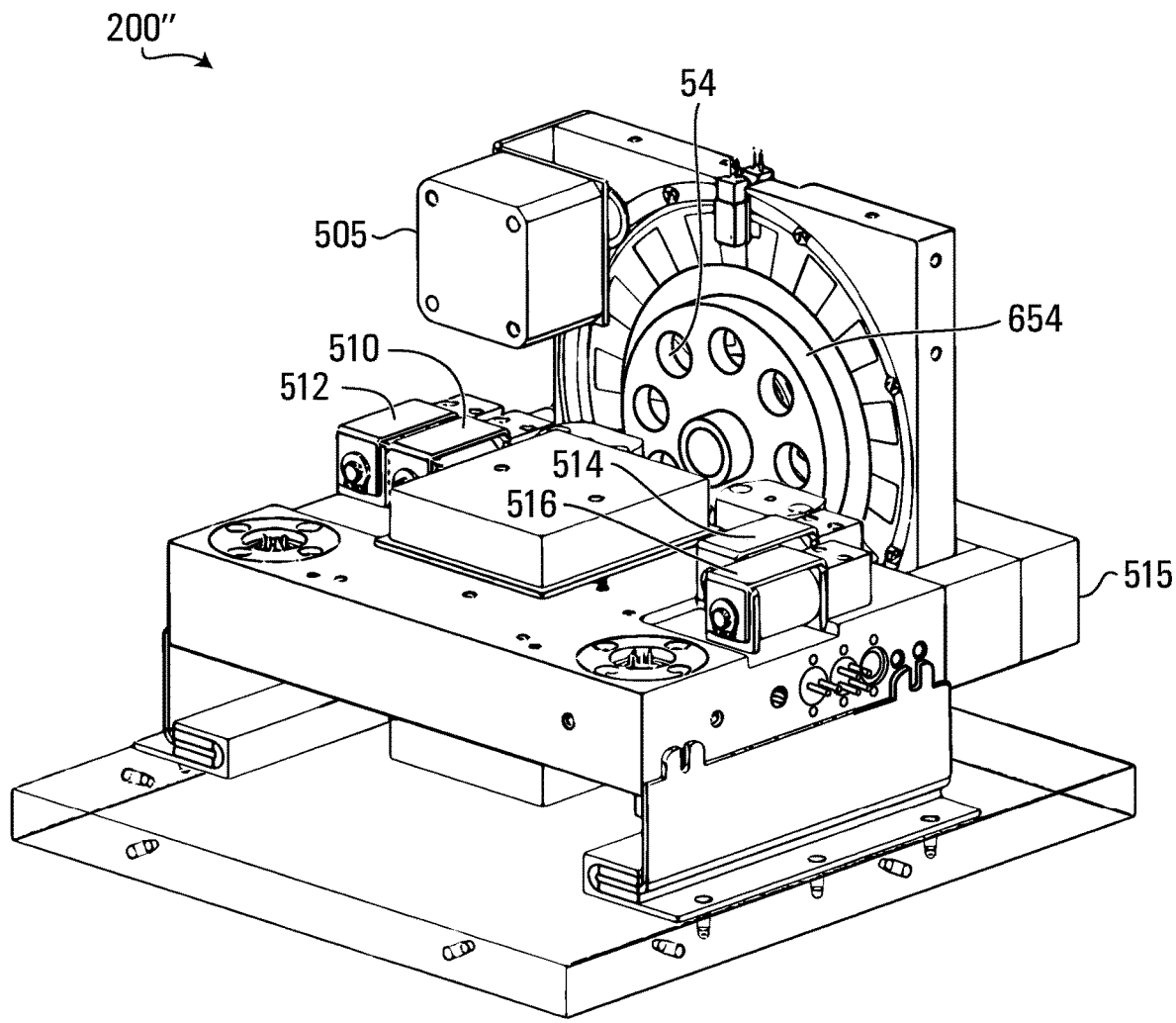
FIG. 7A shows a top front isometric view of a specific practical implementation of an optical absorption measurement system suitable for use in the analyser 20 of the DGA apparatus of FIG. 4 in accordance with a non-limiting example of implementation of the present invention.
Figure 7B:
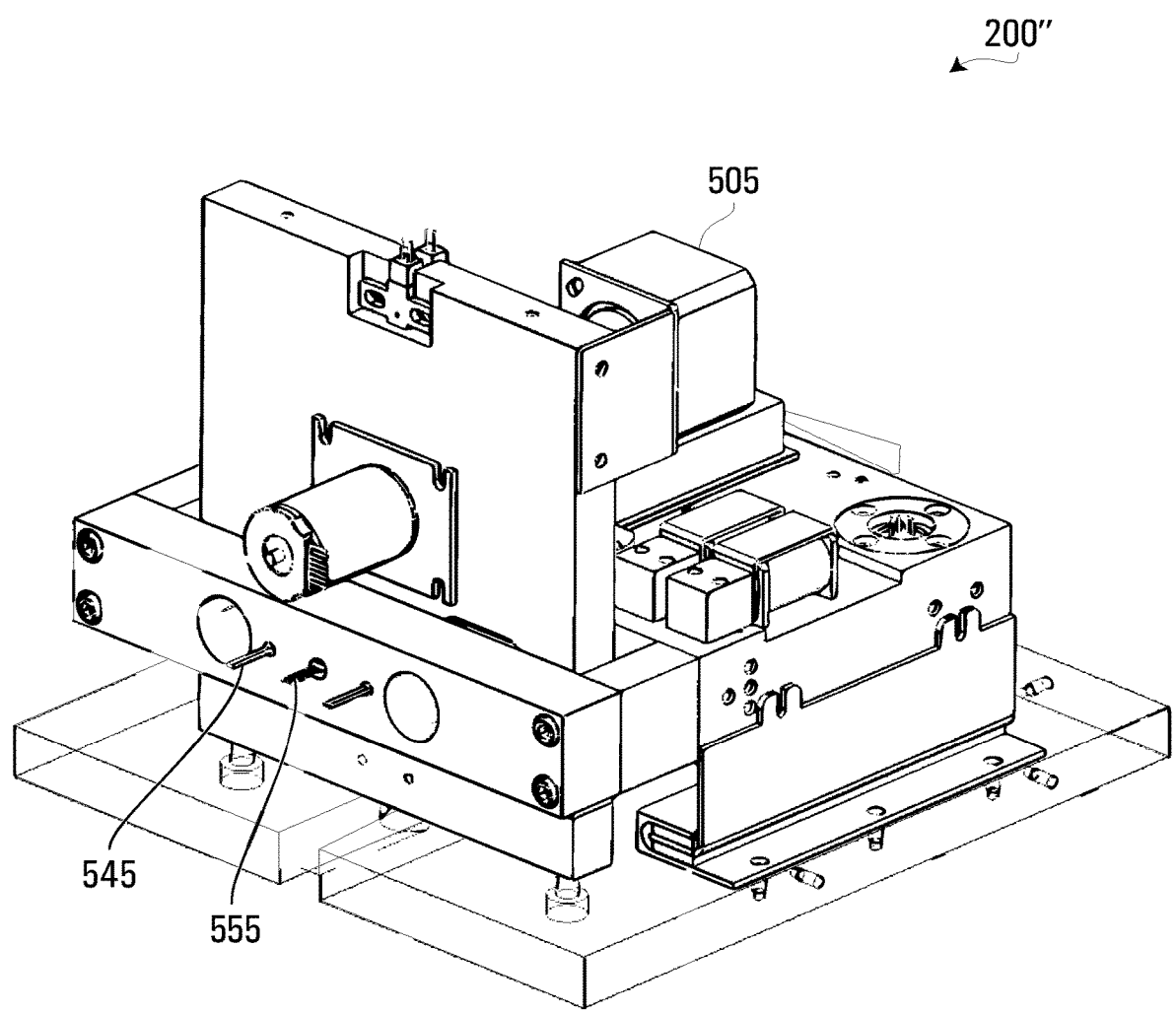
FIG. 7B shows a top rear isometric view of the optical absorption measurement system of FIG. 7A.

FIGS. 7A and 7B show isometric views of a specific practical implementation of an optical absorption measurement system 200" suitable for use in the analyser 20 of the DGA apparatus of FIG. 4 in accordance with a non-limiting example of implementation of the present invention. FIG. 7A shows control valves 510, 512, 514, 516 which control gas transfer into/out of the sample cell 58. In specific examples, such control valves may be solenoid valves or any other suitable type of valves.

The optical absorption measurement system 200 also includes at least one electromagnetic source 48 for generating electromagnetic energy, whereby the electromagnetic energy has wavelengths capable of being absorbed by the specific target gas whose concentration is to be measured inside the sample cell 58.

The selection of the type and characteristic of the electromagnetic energy source 48 depends on the specific target gases whose concentration is to be measured. A target gas will have maximum absorbance of electromagnetic energy at specific wavelengths.

The electromagnetic source 48 may comprise a light emitting diode (LED), a laser, a hot filament, micromachined (MEMS) IR emitter, a halogen lamp and any combination of a light emitting diode (LED), a laser, a hot filament, micromachined (MEMS) IR emitter and a halogen lamp.

Optionally, one or more sensors (not shown) may be provided in association with the electromagnetic source 48 to obtained measurements of the output of the electromagnetic source 48 (intensity, spectral content, etc.), for example by using a second optical detector, such that the measurements may be used by the processing system 240 to take into account changes in the electromagnetic source 48 between the differential measurements taken by detector 66.

In the specific embodiment shown in FIGS. 7A and 7B, the electromagnetic source 48 is conveniently embodied in an electromagnetic source block 515.

Referring to FIG. 7B, in specific embodiments, the optical absorption measurement system 200 may optionally also include a temperature sensor 555 and heater 545 to improve stability of the electromagnetic source 48 by having it mounted into a temperature controlled block.

Catalytic Reactor 60

As described with reference to FIGS. 5 and 6, the optical absorption measurement system 200 200' includes a catalytic reactor 60 configured to apply a catalytic process to the gas in the sample cell 58. Various specific types of catalytic processes may be used and specific catalytic processes may be selected in dependence of the specific target gas species for which information is to be derived. Examples of catalytic processes that may be contemplated include, without being limited to a combustion process and a hydrogenation process. In addition, in some practical implementation, multiple catalytic reactors may be provided (not shown in the Figures) to apply corresponding multiple catalytic processes to the gas in the sample cell 58, either in parallel or in series, in order to modify the concentration of certain specific gas species in the gas in the sample cell 58 and obtain additional optical measurements.

In a specific embodiment in which the catalytic reactor 60 applies a combustion process, the catalytic reactor 60 is configured to combust at least some combustible gases in the gas in the sample cell 58 in a process that consumes $O_2$ and to form combustion by-products including at least one of $H_2O$ and $CO_2$.

In a specific embodiment in which the catalytic reactor 60 applies a combustion process, the catalytic reactor 60 may be specifically configured with suitable mechanical, chemical, temperature and timing properties so as to combust only a subset (including one) of the target combustible species in the gas in the sample cell 58, providing selectivity in the measurement of members of that subset of target gas species as compared to other combustible gas species present.

In another specific embodiment in which the catalytic reactor 60 applies a combustion process, the catalytic reactor 60 may be specifically configured with suitable mechanical, chemical, temperature and timing properties so as to combust different combustible target gas species at different rates. By recording a time-series of optical absorption data during the combustion process, and thereafter interpreting the absorption data using a model of the optical absorption characteristics of the target gases and possibly also the optical absorption characteristics of combustion by-products, and the different combustion rates of the target species, the selectivity of the measurement of concentrations of individual combustible target gas species may be improved. A specific practical example of an application of such an approach is presented later on in the present document.

In some implementations, the catalytic reactor 60 may be controlled by either DC or pulsed power, optionally with temperature or pressure feedback to improve control over reaction rates. Pulsed power and temperature or pressure feedback may serve to prevent possible exothermic runaway of the catalytic reactor 60 and may to allow drying of water formed as part of the combustion reactions. The catalytic reactor 60 may optionally be configured to be operated at different temperatures, for example by providing varying steps of increasing temperature, to selectively react target species. In some alternative implementations, multiple catalytic reactors may be provided to selectively combust different species at different times.

While in the above specific example the catalytic reactor 60 has been described as applying a "combustion process" to combust at least some combustible gases in the gas, it is to be appreciated that combustion is one type of oxidation process that that may be used and that, in alternative implementations, the catalytic reactor 60 may be configured to apply other suitable types of oxidation processes that consume $O_2$.

A specific non-limiting example of a catalytic process based on oxidation that may be used in order to remove acetylene $C_2H_2$ and/or carbon monoxide (CO) from a mixed gas is described in U.S. Pat. No. 4,582,950 issued on Apr. 15, 1986. The contents of this aforementioned document are incorporated herein by reference. It is to be appreciated that this is only a specific non-limiting example and that many other suitable oxidation processes may be used in alternative implementations.

In another example, the catalytic reactor 60 is configured to apply a hydrogenation process configured to consume $H_2$ in the gas in the sample cell 58 and to transform at least some hydrocarbon gases in the gas in the sample cell 58 into other hydrocarbon gases of higher molecular weight.

In some implementations, the catalytic reactor 60 applying the catalytic process may include a catalytic element (not shown in the Figures), such as for example a catalytic surface or other suitable catalytic element, for applying the catalytic process. In some implementations, the catalytic reactor 60 may be configured for heating the catalytic element to initiate or accelerate the catalytic process being applied to the gas in the sample cell 58.

It is to be appreciated that while an oxidation process, including as a specific example a combustion process, and a hydrogenation process have been specifically set forth as examples of catalytic processes that may be considered, it is to be appreciated that other catalytic processes may also be considered in the context of other implementations and that such other processes may become apparent to the person skilled in the art in view of the present description.

Detectors 66

The optical absorption measurement system 200 shown in FIG. 5 also includes at least one detector 66 having a sensing input for obtaining measurements of electromagnetic energy propagated through the gas the sample cell 58, and an output for generating optical absorption signals indicative of optical absorption measurements which are representative of a concentration of a specific target gas being detected.

Some practical detectors 66 may include for example, without being limited to, photo-acoustic, photodetector, thermocouple, thermopile, Golay cell, pyroelectric and combinations of these.

Optical Filter 54

Referring to the embodiment of FIG. 5, the optical absorption measurement system 200 may also include at least one optical filter 54 mounted in the optical pathway 80 between the electromagnetic source 48 and the sample cell 58 for filtering the electromagnetic energy according to a range of wavelengths selected in relation to the specific target gas whose concentration is being measured in the gas in the sample cell 58. The optical filter 54 can be a band pass filter to narrow a range of radiation wavelengths entering the sample cell 58. The optical filter 54 is advantageously used to selectively excite components of the gas in the sample cell 58.

The optical filter 54 may also be configured for allowing different specific wavelengths to be selectively generated in dependence of a selected specific target gas whose concentration is being measured in the gas in the sample cell 58. As an example, FIG. 5 shows a second optical filter 54', where the second optical filter 54' may be configured for filtering the electromagnetic energy according to a range of wavelengths that is different from that of optical filter 54 and selected in relation to another specific target gas whose concentration is being measured in the gas in the sample cell 58. The motor 56 is provided for selectively positioning either optical filter 54 or optical filter 54' in the optical pathway 80. FIG. 7A shows an optical filter wheel 654 including a plurality of optical filters 54, wherein the plurality of optical filters includes optical filters associated to different wavelength to allow preferentially exciting different specific target gases. The optical wheel 654 may be operated with a filter wheel motor 505 as shown in FIG. 7A, so as to control which optical filter 54 to place in the optical pathway of the electromagnetic source.

While the FIG. 7A shows an optical filter wheel 654 containing a plurality of optical filters 54, it is to be appreciated that many other configurations, structures may be contemplated for generating signals of different wavelengths to allow preferentially exciting different specific target gases.

For example, in some specific practical implementations, the optical filters used may be incremental or continuously variable, and may be monochromators, band-pass filters, gratings, interferometers or combinations of these.

In a specific alternative example, not shown in the Figures, the optical filter wheel 654 may alternatively be replaced by one or more one or more tunable optical interferometer assemblies, including for example but without being limited to Fabry-Perot interferometer assemblies, for filtering the electromagnetic energy from the electromagnetic energy source 48. The one or more tunable optical interferometer assemblies may be configured to be adjustable such as to selectively filter frequencies within a frequency range. While the use of discrete optical filters, such as the type that may be used in an optical filter wheel 654, are inherently limited by the number of optical filter 54 to a corresponding number of specific individual frequency bands, tunable optical interferometer assemblies may be dynamically tuned along a continuum of frequencies within a frequency range in a more granular manner than would be allowed with discrete optical filters. As such, the use of this type of device for filtering the electromagnetic energy from the electromagnetic energy source 48 may allow obtaining measurements for a more complete energy absorption spectrum and provide an improved ability to accurately quantify the concentrations of individual target gas species in a gas sample. This may be particularly advantageous in applications in which one or more of the target gas species have absorbing wavelengths which are close to the absorbing wavelengths of other gas species that may be present in the gas sample. Tunable optical interferometer assemblies are known devices in the field of optics and will therefore not be described in further detail here.

In addition to the types of filters that may be contemplated, time series of optical absorption behaviors for gas in the sample cell 58 may be obtained by varying (or scanning through) wavelength-selecting elements such as monochromators and/or tunable interference filters, or by rotating a filter wheel containing fixed bandpass filters and taking multiple optical absorption measurements over time. The manners in which such an approach may be implemented will become apparent to the person skilled in the art and will therefore not be described in further detail here.

Optionally, optical chopping elements may be used including pulsed IR sources, rotating chopper wheels (not shown in the Figures) positioned in the optical pathway 80, and vibrating mechanical choppers (not shown in the Figures), which may in some implementations improve the signal-to-noise ratio.

Gas Extraction System 76

Figure 8:
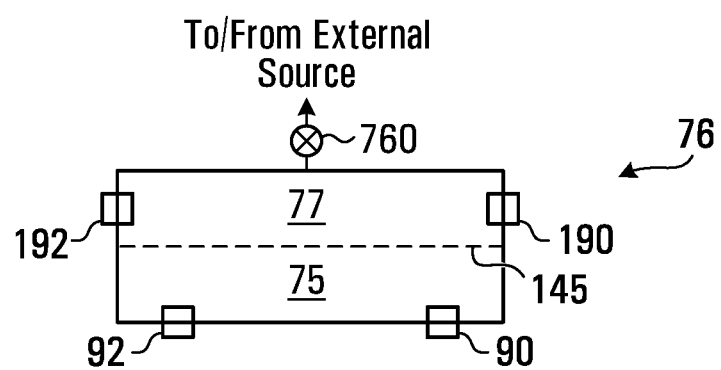
FIG. 8 is a more detailed block diagram of the gas extraction system 76 of the DGA apparatus 100 of FIG. 4 in accordance with a specific non-limiting example of implementation of the present invention.

As can be seen in the specific examples shown in FIGS. 1, 8, the gas extraction system 76 includes a liquid inlet port 90 and a liquid outlet port 92 for connecting to the liquid circulation path 6 which transfers electrical insulating liquid from the electrical equipment 4 to the gas extraction system 76, and from the latter into the former. The gas extraction system 76 also includes fluid outlet port 190 and fluid inlet port 192 mounted thereon for connecting to fluid circulation path 8 which circulates gas extracted from the electrical insulating liquid from the gas extraction system 76 into the analyser 20, and from the latter into the former. It should be noted that the suggested locations of the ports 90, 92, 190 and 192 on the gas extraction system 76 are just exemplifications and, therefore, other connectivity ports and other port locations connected to the gas extraction system 76 can be considered.

The gas extraction system 76 may be configured for extracting gas from the electrical insulating liquid, including for example electrical insulating oil, using any suitable technique known in the art.

In some specific practical implementations, the gas extraction system 76 may extract gas from the electrical insulating liquid using any suitable known head space extraction process. Briefly, headspace extraction is achieved by the diffusion of dissolved gases into the gas phase at constant temperature and pressure conditions until the equilibrium of coexistent phases is established. Optionally, elements for mechanically agitating the gas extraction system 76 may be provided in the apparatus 100 for accelerating the extraction of gases from the electrical insulating liquid.

In other specific practical implementations, the gas extraction system 76 may extract gas from electrical insulating liquid 75 using a semipermeable barrier 145 enclosed within the gas extraction system 76, as illustrated in FIG. 8. The semipermeable barrier 145 is configured to preferentially permeate one or more components into the gas extraction space 77, such as gases and moisture from the electrical insulating liquid while simultaneously restraining the permeation of one or more other components, such as heavy hydrocarbon gases, electrical insulating liquid molecules, and droplets, into the gas extraction space 77. Advantageously, the use of such semipermeable wall 145 can help reduce or prevent exposure of optical components of the analyser 20 to damaging components present in the electrical insulating liquid, for example heavy hydrocarbons, thereby improving apparatus stability over time.

In one practical embodiment, the semipermeable barrier 145 may include a semi-permeable membrane which permeates gases but not transformer insulating liquids. Various geometries and physical constructions for the semipermeable barrier 145 will become apparent to the person of skill in the art in view of the present disclosure. Examples of such semi-permeable membranes are known in the art and, for the purpose of conciseness, will not be further described here.

The gas extraction system 76 may be configured for extracting from the electrical insulating liquid a quantity of gas that may vary according to specific implementations. In some non-limiting examples, the extracted gas may have a volume of less than 10 cubic centimeters (10 cc) and preferably between 3 cc and 10 cc. It is to be appreciated that other suitable volumes may also be contemplated in alternative implementations.

Other configurations useful for extracting dissolved gas from a liquid can be used in the apparatus 100 and will become apparent to the person of skill in the art in view of the present disclosure.

When extracting gas from a sample of electrical insulating liquid taken from a piece of electrical equipment, it has been observed that the total pressure of the extracted gas can vary significantly, e.g., from 1 to 16 pounds per square in absolute (PSIA), depending on the design, history and operational conditions of the piece of electrical equipment.

Adjusting Pressure and Temperature Characteristics

Because the absorption response of each gas species in a gas mixture may change with total pressure and/or of the mixture, the precision and accuracy of the optical absorption measurements may be affected by pressure and/or temperature variations. Managing such gas pressure and/or temperature variability can, thus, have particular advantages in improving accuracy of the gas detection/quantification with the apparatus 100.

In order to account for and manage these pressure and/or temperature variations, a first approach may be to calibrate the pressure and/or temperature dependence the apparatus 100 so that pressure and/or temperature compensation may subsequently be applied to the measurements.

Another (second) approach to manage these pressure and/or temperature variations is to adjust the pressure and/or temperature in the extraction space 77 of the gas extraction system 76 (see FIG. 8) so that the pressure and/or temperature of the gas sample lies within corresponding narrower ranges. By setting that narrower pressure and/or temperature ranges to the pressure and/or temperature at which the apparatus 100 was calibrated and characterized, more precision and accuracy in the measurements of gas concentrations can be achieved.

In some specific practical implementations, the gas extraction system 76 may be provided with a pressure regulating system including a pressure regulating element 760 for mixing an external gas with the gas sample the extraction space 77 extracted from the sample of the electrical insulating liquid to obtain a mixed-gas sample such that the mixed-gas sample has a pressure approaching a target pressure. The pressure regulating element 760 may be in communication with an external reference gas source, such as for example a tank containing Nitrogen, or alternatively, the pressure regulating element 760 may be in communication with ambient air. While a specific location for one pressure regulating element 760 is shown in the figures, it will be apparent to the person of skill that other suitable locations and/or more than one pressure regulating element 760 may be present depending on specific applications.

In some specific embodiments, the target pressure may be, for example but not limited to, between 8 to 17 PSIA; preferable between 13 to 17 PSIA.

In some specific non-limiting embodiments, the target pressure may be near atmospheric pressure. It is to be appreciated that atmospheric pressure may vary in dependence of the altitude at which the apparatus 100 is installed. For example, the apparatus may be configured and calibrated to be installed at a specific geographical location and, as such, the target pressure would be near the atmospheric pressure at the specific geographical location.

As mentioned above, in some embodiments, the external gas mixed with the gas sample extracted from the sample of the electrical insulating liquid may be ambient air. In such embxximents, the pressure regulating element 760 may mix ambient air with the gas extracted from the liquid in such a manner that the total pressure of the extracted gas (mix) is close to atmospheric pressure while the fault gas concentrations in the gas are close to equilibrium with the liquid. An advantage of using ambient air, in contrast to other possible gases, is that it is readily and freely available.

The pressure regulating element 760 may be an active pressure regulating element or alternatively may be a passive pressure regulating element.

In a specific practical implementation of an active pressure regulating element, the pressure regulating element 760 may include for example any suitable set of actionable valves and conduits known in the art for channeling an external gas into the head space 77 of the gas extraction system 76 until the gas extraction system 76 approach the target pressure.

Similarly, the gas extraction system 76 may be equipped with a suitable temperature regulating system configured to heat (or cool) the gas extraction system 76 until the gas extraction system 76 approach the target temperature.

In some embodiments, instead of, or in addition to, the optical absorption measurement system 200 is configured for managing pressure and/or temperature characteristics of the gas in the sample cell 58, to adjust the pressure and/or temperature in the sample cell 58 (see FIGS. 5 and 6) so that the pressure and/or temperature of the gas sample lies within corresponding narrower ranges. Moreover, the optical absorption measurement system 200 may be configured for managing pressure and/or temperature characteristics of the gas in the sample cell 58, to adjust the pressure and/or temperature in the sample cell 58 (see FIGS. 5 and 6) so that the pressure and/or temperature characteristics of the gas in the sample cell 58 prior to and after application of a catalytic process by the catalytic reactor 60 lies within similar ranges.

In this regard, the optical absorption measurement system 200 may include a pressure regulating element (not shown in the Figures) configured to introduce an external gas to the sample cell 58 to obtain a mixed-gas, wherein the obtained mixed-gas has a pressure approaching a target pressure. Different types of external gases may be used in practical implementations including, without being limited to, ambient air, dry air and Nitrogen ($N_2$). Similarly, the optical absorption measurement system 200 configured to heat (or cool) the gas sample cell 58 so that the gas held in the sample cell approaches a target temperature.

Dissolved Gas Analysis Process

The apparatus 100 is configured for performing dissolved gas analysis on the piece of electrical equipment 4 having components immersed in electrical insulating liquid.

Figure 9:
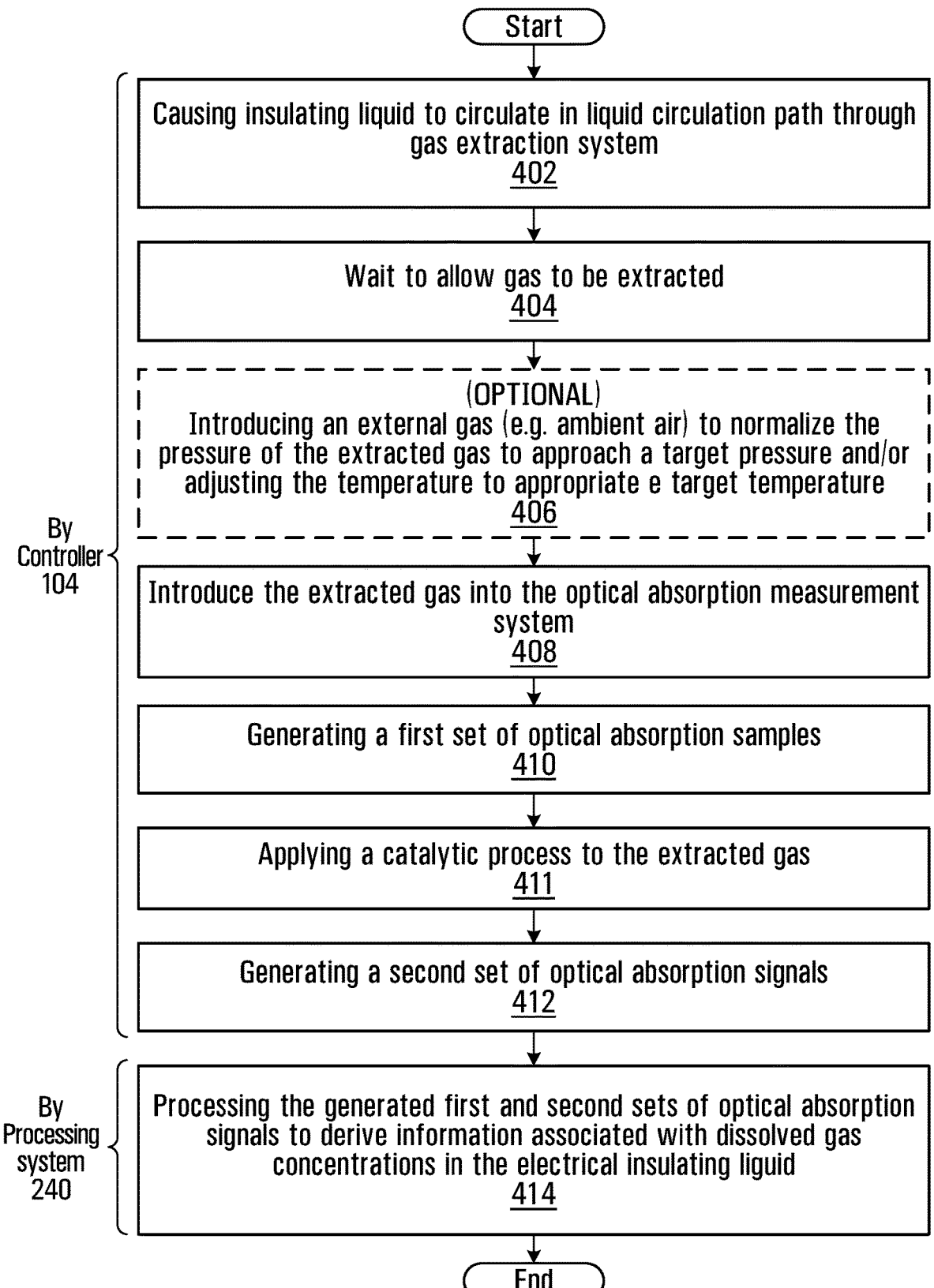
FIG. 9 is a flow diagram of a process implemented by the DGA apparatus 100 shown in FIG. 4 in accordance with a non-limiting example of implementation of the present invention.

A very specific process that may be implemented by apparatus 100 is shown in FIG. 9.

With reference to FIG. 9, at step 402, electrical insulating liquid is caused to circulate through liquid circulation path 6 using pump 40 so that the insulating liquid goes through the gas extraction system 76.

At step 404, the system waits for a certain time delay to elapse to allow gas from the insulating liquid to be extracted by the gas extraction system 77. Once the certain period of time has elapsed, the method then proceeds to optional step 406 or to step 408.

At optional step 406, temperature and/or pressure characteristics of the extracted gas are adjusted to approach a target pressure and/or a target temperature. In particular, optional step 406 may include using the pressure regulating element 760 to introduce an external gas into the gas extracted from the electrical insulating liquid to normalize the pressure so that the mixed-gas sample has a pressure approaching the target pressure. Optional step 406 may also include, using a temperature regulation element (not shown in the figures) to heat (or cool) the gas extracted from the electrical insulating liquid to normalize the temperature so that the gas has a temperature approaching the target temperature. The method then proceeds to step 408.

At step 408, the extracted gas is introduced into the optical absorption measurement system 200. The method then proceeds to step 410.

At step 410, the gas in the sample cell 58 of the optical absorption measurement system 200 is excited using an electromagnetic energy source to produce a first set of IR absorption signals associated with the gas sample. The gas may be excited at one or more specific energy bands (for example by selecting appropriate filters) in order to target specific gas species in the gas in the sample cell 58.

At step 411, a catalytic process is applied by the catalytic reactor 60 the gas to derive a modified gas. The type and manner of applying the catalytic process applied may vary in dependence of the nature of the gas species that it is desirable to derive information.

At step 412, the gas in the sample cell 58 of the optical absorption measurement system 200, which is a modified gas following step 411, is excited using the electromagnetic energy source to produce a second set of IR absorption signals associated with the modified extracted gas sample. The modified gas may be excited the same at one or more specific energy bands as those used at step 411 in order to target specific gas species in the gas in the sample cell 58.

At step 414, the first and second sets of optical absorption signals associated with the gas sample derived at step 410 are processed with the processing system 240 using suitable differential calculation/modeling approaches in order to derive information conveying concentrations of specific gas species present in the gas sample and/or to derive information conveying a fault status (or alternatively a fault level ranking) of the electrical equipment 4. The specific differential calculation/modeling approaches used in different implementations may differ and will depend on a number of factors which may include, without being limited to, the configuration of the optical components of the apparatus, the specific target species whose concentration is being measured, the type of catalytic process used and the manner in which it is applied. Specific suitable differential calculation/modeling approaches that may be used in practical implementations will become apparent to the person skilled in the art in view of the present description and as such will not be described in further detail here.

In some implementation, the calculations performed at step 414 made by processing the first and second sets of optical absorption signals may leverage absorption reductions when a combustible gas species is combusted, or the absorption increase when the by-products of combustion are formed, or both, to derive information conveying concentrations of specific gas species present in the gas sample. Depending on the other species in the gas mixture, and the optical spectral regions chosen for the measurements (by selecting suitable filters), the absorption reduction or the absorption increase may occur in spectral regions in which there are fewer interferences between gas species in the mixed gas sample. As a result, a system providing increased sensitivity and accuracy of measurements of the concentration of the target gases may be obtained.

For example, $CO_2$ is formed when a combustion process is applied to combustible gases, which generates a large absorption signal in a spectral region near 4.2 micrometers that is relatively free of interference absorption by other gases. To leverage the $CO_2$ absorption increase signal, a data analysis model applied at step 414 may be configured to anticipate possible catalytic reactions that may occur within the sample and leading to the generation of CO2. Specific examples will be described later below in the present document to illustrate such modelling.

Specific gas species whose concentration may be measured include one or more of the following: carbon dioxide ($CO_2$), carbon monoxide (CO), ethane ($C_2H_6$), methane ($CH_4$), ethylene ($C_2H_4$) and acetylene ($C_2H_2$). The concentrations of the dissolved gas species above may be reported in "parts per million" by volume (ppm) at a given temperature and pressure, commonly 0 degrees Celsius and 14.6 PSIA. For example, in a practical implementation, the processing system 240 may be configured to detect/quantify one or more of dissolved gas concentrations of at least 2 ppm CO (e.g., 2-50,000 ppm); at least 20 ppm $CO_2$ (e.g., 20-50,000 ppm); at least 2 ppm $CH_4$ (2-50,000 ppm); at least 0.5 ppm $C_2H_2$ (e.g., 0.5-50,000 ppm); at least 2 ppm $C_2H_6$ (e.g., 2-50,000 ppm); at least 2 ppm $C_2H_4$ (e.g., 2-50,000 ppm).

As shown in FIG. 9, in some implementations, steps 402 404 406 408 410 411 412 may be performed by the controller 104 and step 414 may be performed by the processing system 240.

Other practical examples of implementations will become apparent to the reader in view of the teachings of the present description and as such, will not be further described here.

Some Advantages that May be Achieved by Certain Embodiments

Some practical implementations of the apparatus 100 may provide one or more of the following advantages, amongst possible others, over conventional GIRAS approaches and other optical absorption schemes:

Advantage 1: Improved sensitivity (lower detectable limit of concentrations) of GIRAS methods by revealing changes in optical absorption associated specifically with the combustion of target combustible gas species in the gas mixture to be analysed, reducing (or eliminating) "offset" differences that may arise in other differential methods where intentional apparatus differences, such as changes in optical filters, tunable filter settings, and/or different optical paths are used to obtain the different optical absorption measurements that are used in the differential method/model.

Advantage 2: Improved selectivity (between gases in a given spectral region) by measuring changes in optical absorption before and after a combustion process, even if the gas under analysis contains gases with optical absorption properties that overlap with those of a target gas species and would otherwise interfere with the measurement. This can be particularly helpful when the optical absorption of non-combustible or lesser-combusted gas species is large or comparable to that of a target species.

Advantage 3: The spectral absorption of the combustion by-products may be stronger than that of the target species being combusted, and may be used to achieve a larger signal to noise and thereby improve sensitivity to the target gas species, particularly if the combustion model in the analysis anticipates both the absorption loss of the combusted species and the absorption increase from the combustion by-products. The spectral absorption of the by-products may also be in a spectral region which is has smaller interfering absorption signals, also helping to improve the sensitivity to the target gas species.

Advantage 4: For some applications, the advantages of increased sensitivity and selectivity may allow gas detecting and measuring objectives to be achieved using simpler, more reliable and lower cost GIRAS methods and apparatus.

Specific Examples of Application in DGA

In the present section, specific examples of us of the apparatus 100 described above and/or of the analyser 20 (shown in FIG. 4) will be described for the purpose of illustrating a few of the various practical applications of the solution set forth in the present document. It is to be expressly understood that these are only examples and that many other applications are possible.

Figure 12:
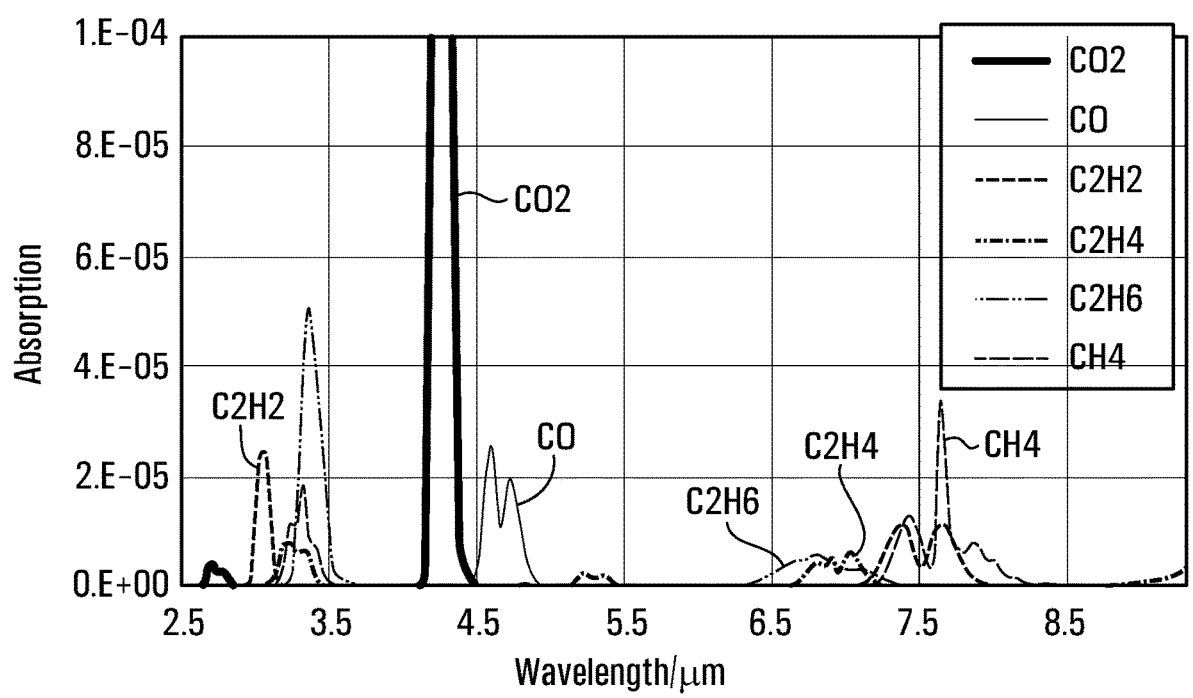
FIG. 12 is a diagram showing absorption spectra for typical DGA gases including $CO_2$, CO, $C_2H_2$, $C_2H_4$, $C_2H_6$ and $CH_4$.

These examples set forth are primarily in the DGA space and focus on the capability of measuring concentrations of fault gases such as $CO_2$, CO, $C_2H_2$, $C_2H_4$, $CH_6$, and $CH_4$. FIG. 12 is a diagram showing an absorption spectrum for typical DGA gases including $CO_2$, CO, $C_2H_2$, $C_2H_4$, $C_2H_6$ and $CH_4$, which will be useful in appreciating the functionality that may be provided by embodiments of the apparatus 100 to discriminate between these gas species.

Example 1

In a dissolved gas analysis application (DGA) application, $C_2H_2$ is a key gas associated with serious transformer faults. It is of interest to measure dissolved $C_2H_2$ gas concentrations smaller than 1 ppm (microliters of $C_2H_2$ at 0° C. and 101.325 kPa per liter of oil) with on-line monitors designed to detect and diagnose transformer faults.

Accounting for the solubility of $C_2H_2$ in mineral oil, this implies we would like to accurately measure concentrations of $C_2H_2$ in a gas sample extracted from the oil, with sensitivity smaller than 1 ppm (micromoles of $C_2H_2$ per mole of total gas). To measure such small concentrations of $C_2H_2$ by GIRAS methods, a strong absorption band is desirable.

$C_2H_2$ has a strong IR absorption band near the wavelength of 3.1 micrometers. Water vapour also exhibits absorption in this region. For a spectral width of 0.07 micrometers centered at 3.1 micrometers, the IR absorption of water vapour is approximately 500 times smaller than that of $C_2H_2$ (for the same molar concentration of each).

However, for a transformer with insulating liquid nearly saturated with dissolved moisture, the concentration of water vapour in the gas sample extracted from the liquid can be 50,000 ppm (micromoles of $H_2$) per mole of total gas).

In that case, the absorption signal from 1 ppm $C_2H_2$ is approximately 100 times smaller than that from the water vapour. Also, the amount of water vapour in the sample is expected to vary on a regular basis depending on the load and other operating conditions of the transformer.

The combustion assisted differential method allows isolation of the small signal from the $C_2H_2$ against the strong and variable IR absorption interference form water vapour.

Example 2

Based on the stoichiometry of the chemical reaction, combustion of 1 ppm $C_2H_2$ (micromoles of $C_2H_2$ per moles of total gas) leads to the formation of 2 ppm of $CO_2$ (micromoles of $CO_2$ per moles of total gas). $CO_2$ has a strong absorption band near 4.25 micrometers.

The absorption increase from adding 2 ppm $CO_2$ to the system through a combustion process (i.e. the catalytic reactor applies a combustion process), is approximately 25 times larger than the absorption decrease associated with the elimination of 1 ppm of $C_2H_2$, if we consider spectral filter widths of 0.07 micrometers centered on the $CO_2$ band at 4.25 micrometers and the $C_2H_2$ band at 3.1 micrometers.

As such, by using the pre-combustion optical absorption signals and the post-combustion optical absorption signals and processing them using a model description of the combustion process, the absorption increase near 4.25 micrometers can be used when quantifying the amount of combusted $C_2H_2$ target gas. Beneficially for the signal-to-noise, the $CO_2$ band near 4.25 micrometers is relatively free from interferences from moisture or other potentially interfering species of concern in conventional transformer gas applications.

Example 3

Some types of catalytic reactor based on tin-oxide (SnO) or silver-oxide ($Ag_2O$) for example may be heated to temperatures where gas species $H_2$, CO and $C_2H_2$ are combusted much more quickly than $CH_4$, $CH_4$ and $C_2H_6$ gas species.

As will be apparent, CO, $C_2H_2$, $CH_4$, $C_2H_4$ and $C_2H6$ gas species generate $CO_2$ when they are combusted with $O_2$. The increase in $CO_2$ IR absorption early during a (catalytic) combustion process can be attributed primarily to the combustion of CO and $CH_2$. The amount of $CO_2$ IR absorption increase near 4.25 micrometers generated by the combustion of CO can be estimated from the amount of CO IR absorption lost near 4.7 micrometers. Since the $CO_2$ IR absorption near 4.25 micrometers is both stronger than that of $C_2H_2$, near 3.1 micrometers, and also in a spectral region near 4.25 micrometers exhibits less interference from water vapour and other compounds, the amount of increased $CO_2$ IR absorption can provide more precise and/or accurate information about the concentration of $C_2H_2$ present in the sample before the reaction.

In as specific implementation, by deriving a time-series of IR absorption signals/measurements while the combustion process is being applied as well as after its completion, the signals/measurements may be processed the processing system 240 using a model of the IR absorption characteristic of each species (i.e. CO, $C_2H_2$, $CH_4$, $C_2H_4$ and $C_2H_6$ gas species), and a model for the combustion process and combustion rate of each species. In this manner, the process and apparatus 100 described in the present document can be used to improve the selectivity for $C_2H_2$ even if the combustion rate of $C_2H_2$ is not dramatically faster than that of $CH_4$, $C_2H_4$ and $C_2H_6$.

Other Examples

Fault gas species $CH_4$, $C_2H_2$, $C_2H_4$ and $C_2H_6$ are typically considered to be of interest for dissolved gas analysis applications used in connection with transformers and other pieces of electrical equipment. These species have relatively strong absorption signals in the spectral region from 3.0 to 3.4 micrometers (wavelength). However water vapour and heavier hydrocarbon gases may also be present in gas samples extracted from transformer oil, and these compounds also exhibit significant IR absorption in this same spectral region. The proposed method using a catalytic reactor applying a combustion process to the gas under analysis can improve the selectivity of IR methods to quantify the concentrations of the above fault gas species in applications where the extracted gas contains humidity and heavy hydrocarbon gases.

$C_2H_4$ has a strong absorption band near 10 micrometers. This band is attractive for the measurement of $C_2H_4$ because it is separate from the IR absorption bands of the other transformer fault gases ($CH_4$, $C_2H_2$ and $C_2H_6$).

However $SF_6$ gas is commonly used in high voltage bushings on transformers and it can leak into transformer oil over time. The $SF_6$ gas exhibits IR absorption that overlaps with the $C_2H_4$ absorption band near 10 micrometers. So, if the band near 10 micrometers is being used to quantify a $C_2H_4$ concentration in the gas, $SF_6$ leaking into the transformer oil will cause false high readings of $C_2H_4$.

However, since $SF_6$ is not a combustible gas, the use of a catalytic reactor applying a combustion process in a device of the type described in the present document may allow obtaining differential measurements in the band near 10 micrometers (for example by obtaining absorption measurements prior to combustion and absorption measurements during and/or after combustion). By programming the processing system 240 to process these differential measurements, it becomes possible to discriminate between the absorption contributions of the combination of $C_2H_4$ and $SF_6$ and that of $SF_6$ without $C_2H_4$, thus allowing obtaining more accurate measurements for the $C_2H_4$ concentration.

In addition, this approach may also permit detection of the presence of an $SF_6$ leak when an IR absorption signal in this spectral region (in the band near 10 micrometers) is high and is substantially unchanged by the application of the combustion process.

Practical Example of Implementation for Processing System 240

Those skilled in the art should appreciate that in some non-limiting embodiments, all or part of the functionality previously described herein with respect to the processing system 240 of the apparatus 100 for providing the dissolved gas analysis functionality as described throughout this specification, may be implemented using pre-programmed hardware or firmware elements (e.g., microprocessors, FPGAs, application specific integrated circuits (ASICs), electrically erasable programmable read-only memories (EEPROMs), etc.), or other related components.

In other non-limiting embodiments, all or part of the functionality previously described herein with respect to the processing system 240 of the apparatus 100 may be implemented as software consisting of a series of program instructions for execution by one or more computing units. The series of program instructions can be tangibly stored on one or more tangible computer readable storage media, or the instructions can be tangibly stored remotely but transmittable to the one or more computing unit via a modem or other interface device (e.g., a communications adapter) connected to a computer network over a transmission medium. The transmission medium may be either a tangible medium (e.g., optical or analog communications lines) or a medium implemented using wireless techniques (e.g., microwave, infrared or other transmission schemes).

Those skilled in the art should further appreciate that the program instructions may be written in a number of suitable programming languages for use with many computer architectures or operating systems.

Figure 10:
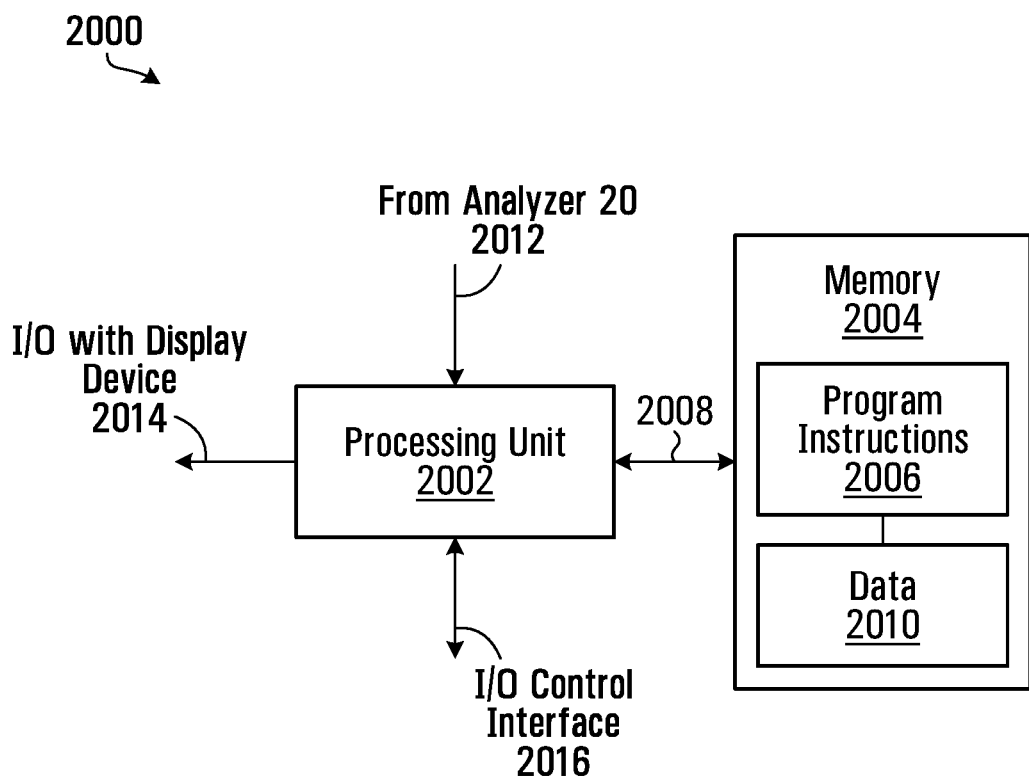
FIG. 10 is a block diagram of an apparatus suitable for implementing the processing system 240 of the DGA apparatus 100 of FIG. 4 in accordance with a specific example of implementation of the present invention.

In a non-limiting example, some or all the functionality of the processing system 240 may be implemented on a suitable microprocessor 2000, of the type depicted in FIG. 10. Such a microprocessor 2000 typically includes a processing unit 2002 and a memory 2004 that is connected by a communication bus 2008. The memory 2004 includes program instructions 2006 and data 2010. The processing unit 2002 is adapted to process the data 2010 and the program instructions 2006 in order to implement the functionality described and depicted in the drawings with reference to the processing system 240. The microprocessor 2000 may also comprise one or more I/O interfaces for receiving or sending data elements to external modules. In particular, the microprocessor 2000 may comprise an I/O interface 2012 with the analyzer 20 of the apparatus 100 (shown in FIG. 1), an I/O interface 2014 for exchanging signals with an output device (such as a display device) and an I/O interface 2016 for exchanging signals with a control interface (not shown).

General System for Providing DGA Monitoring and Analysis Functionality

The person skilled in the art will appreciate that, while the block diagram of the apparatus 100 depicted in FIG. 4 has shown some features for performing dissolved gas analysis on a piece of electrical equipment, it is to be appreciated that such features may constitute but a subset of the features within an actual commercial DGA apparatus.

Figure 11:
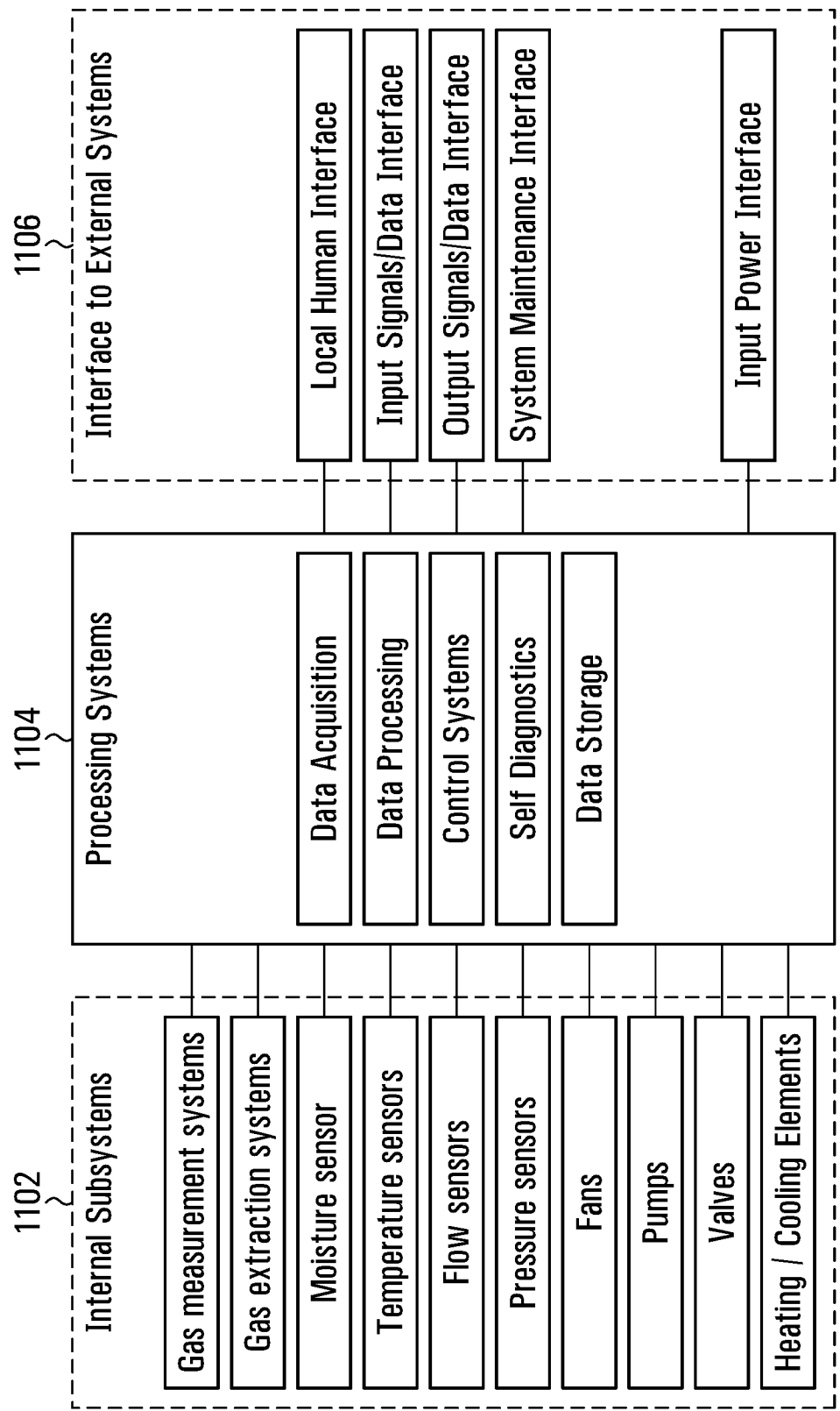
FIG. 11 is a block diagram showing three types of subsystems (internal 1102, processing systems 1104 and interfaces to external system 1106) interconnected to one another to provide DGA monitoring and analysis functionality, including functionality provided by the DGA apparatus depicted in FIG. 4, in accordance with a non-limiting example of implementation of the present invention.

FIG. 11 is a block diagram showing three types of subsystems (internal 1102, processing systems 1104 and interfaces to external system 1106) interconnected to provide DGA monitoring and analysis functionality. The subsystems may have many interconnections and data and control signals flow in both directions between many of them—these have been omitted for the purpose of clarity in the figure.

As depicted, internal subsystems 1102 may include, without being limited to, heating/cooling elements, flow sensors, temperature sensors, moisture sensors, other (complementary) gas measurement systems, other gas extraction systems, fans, pumps, valves, pressure sensors.

As depicted, the processing system 1104 may include, without being limited to, data acquisition, data processing (which may implement the functionality of processing system 240 described above), control, self-diagnostics and data storage.

In addition, also as depicted, the interfaces to external systems 1106 may include, without being limited to, one or more local human interfaces, input signal/data interfaces, output signal/data interfaces, system maintenance interface and input power interfaces. The human interface may include any suitable display and/or illuminated indicators, and/or buttons and/or touch screen. Input signal/data interfaces may include interfaces for signals from external sensors (e.g. analogue inputs), and/or digital communications to effect the operation of the system. Output signal/data interfaces may include for example logic-level outputs (relays), analogue outputs and/or digital communications. The digital communications may be carried by copper, optical fiber, or wireless media, or any combination thereof. The digital communications may include, without being limited to, the use of Ethernet or Serial communication protocols, and may include the use of industrial communication protocols such as DNP3, Modbus, IEC 61850. The signals being sent/received through these interfaces (local human interfaces, input signal/data interfaces, output signal/data interfaces) may convey (for example but without being limited to) system status, system settings, measured concentrations and rates of change of concentrations of the dissolved gases and moisture in the insulating liquid, status of dissolved gas and/or moisture levels and rates of change in relation to pre-set thresholds, interpretations of dissolved gas and/or moisture levels based on algorithms adapted to that purpose, and system events. The system maintenance interface may include a digital communication interface to enable firmware updates and settings updates, for example. In addition, the input power interface may in some implementations be configured to monitor power quality, filter the incoming power, control conducted emissions, and protect the system from voltage spikes and power dropouts.

It will be appreciated by the person skilled in the art in view of the present description that the subsystems depicted in FIG. 11 have been shown for the purpose of illustration only and that a detailed description of these subsystems is beyond the scope of the present application and will thus not be described in further detail here.

Note that titles or subtitles may be used throughout the present disclosure for convenience of a reader, but in no way these should limit the scope of the invention. Moreover, certain theories may be proposed and disclosed herein; however, in no way they, whether they are right or wrong, should limit the scope of the invention so long as the invention is practiced according to the present disclosure without regard for any particular theory or scheme of action.

All references cited throughout the specification are hereby incorporated by reference in their entirety for all purposes.

It will be understood by those of skill in the art that throughout the present specification, the term "a" used before a term encompasses embodiments containing one or more to what the term refers. It will also be understood by those of skill in the art that throughout the present specification, the term "comprising", which is synonymous with "including," "containing," or "characterized by," is inclusive or open-ended and does not exclude additional, un-recited elements or method steps.

Unless otherwise defined, all technical and scientific terms used herein have the same meaning as commonly understood by one of ordinary skill in the art to which this invention pertains. In the case of conflict, the present document, including definitions will control.

As used in the present disclosure, the terms "around", "about" or "approximately" shall generally mean within the error margin generally accepted in the art. Hence, numerical quantities given herein generally include such error margin such that the terms "around", "about" or "approximately" can be inferred if not expressly stated.

Although various embodiments of the disclosure have been described and illustrated, it will be apparent to those skilled in the art in light of the present description that numerous modifications and variations can be made. The scope of the invention is defined more particularly in the appended claims.

What is claimed is:

1. An apparatus for performing dissolved gas analysis on a piece of electrical equipment having components immersed in electrical insulating liquid, the apparatus comprising:
    a) a gas extraction system for extracting gas from the electrical insulating liquid, said gas extraction system including at least one of:
        a structure defining a gas extraction space above at least a portion of the electrical insulating liquid to extract gas from the electrical insulating liquid by diffusion; and
        a semi-permeable membrane forming a phase barrier between at least a sample of the electrical insulating liquid and a gas extraction volume, the semi-permeable membrane allowing one or more gas components in the electrical insulating liquid to permeate into the gas extraction volume while restraining permeation of one or more other components;
    b) an analyser in fluid communication with said gas extraction system for performing gas analysis on the extracted gas, said analyser including an optical absorption measurement system configured to excite the extracted gas with one or more electromagnetic energy sources and to obtain optical absorption signals associated with the extracted gas:
        i) prior to application of a catalytic process to the extracted gas; and
        ii) during and/or after application of the catalytic process to the extracted gas;
    c) a processing system programmed for deriving information associated with dissolved gas concentrations in the electrical insulating liquid at least in part by processing the optical absorption signals obtained by the analyser.

2. An apparatus as defined in claim 1, wherein the gas extraction system includes the structure defining the gas extraction space above at least the portion of the electrical insulating liquid to extract gas from the electrical insulating liquid by diffusion.

3. An apparatus as defined in claim 1, wherein the gas extraction system includes the semi-permeable membrane forming the phase barrier between at least the sample of the electrical insulating liquid and the gas extraction volume.

4. An apparatus as defined in claim 1, wherein said apparatus comprises a liquid inlet and a liquid outlet connectable to the piece of electrical equipment for allowing electrical insulating liquid to circulate between the piece of electrical equipment and the apparatus through a liquid circulation path, said gas extraction system being in communication with the liquid circulation path.

5. An apparatus as defined in claim 1, wherein the derived information conveys a concentration of a specific target gas in the extracted gas.

6. An apparatus as defined in claim 1, wherein processing the obtained optical absorption signals to derive information comprises:
    a) deriving concentrations of different component species in the extracted gas;
    b) assessing the derived concentrations of the different component species to derive diagnostic information.

7. An apparatus as defined in claim 1, wherein the optical absorption measurement system includes a catalytic reactor configured to apply the catalytic process to the extracted gas.

8. An apparatus as defined in claim 1, wherein the catalytic process includes heating a catalytic element to initiate or accelerate the catalytic process.

9. An apparatus as defined in claim 1, wherein the optical absorption measurement system is configured for adjusting temperature and pressure characteristics of the extracted gas so that the optical absorption signals are obtained at similar temperatures and pressures.

10. An apparatus as defined in claim 1, wherein the gas extraction system includes the semi-permeable membrane for extracting gas from the electrical insulating oil.

11. An apparatus as defined in claim 1, wherein the extracted gas that said gas extraction system is configured for extracting from the electrical insulating liquid has a volume of less than 10 cubic centimeters.

12. An apparatus as defined in claim 1, wherein the information associated with the dissolved gas concentrations in the insulating liquid derived by the processing system conveys concentrations of one or more specific gases selected from the group consisting of carbon dioxide ($CO_2$), carbon monoxide (CO), ethane ($C_2H_6$), methane ($CH_4$), ethylene ($C_2H_4$) and acetylene ($C_2H_2$).

13. An apparatus as defined in claim 1, wherein said optical absorption measurement system includes a plurality of optical filters for filtering the electromagnetic energy from the one or more electromagnetic energy sources, the optical filters in the plurality of optical filters being associated with respective frequency bands corresponding to specific target gases.

14. An apparatus as defined in claim 1, wherein said piece of electrical equipment includes at least one of a transformer, a tap-changer and a circuit breaker.

15. An apparatus as defined in claim 1, wherein at least one of the one or more electromagnetic energy sources is an IR electromagnetic energy source and wherein the optical absorption signals are IR absorption signals.

16. An apparatus as defined in claim 1, wherein at least one of the one or more electromagnetic energy sources is an UV electromagnetic energy source and wherein the optical absorption signals are UV absorption signals.

17. An apparatus as defined in claim 1, wherein said apparatus is configured for establishing a communication link over a computer network with a remote computing device for transmitting the derived information associated with dissolved gas concentrations in the electrical insulating liquid.

18. An apparatus as defined in claim 17, wherein the remote computing device is a smartphone.

19. An apparatus as defined in claim 1, wherein the catalytic process includes at least one of a combustion process and a hydrogenation process.

20. An apparatus as defined in claim 19, wherein the catalytic process includes a combustion process.

21. An apparatus as defined in claim 20, wherein the combustion process is configured to combust at least some combustible gases in the extracted gas in a process that consumes $O_2$ and forms combustion by-products including at least one of $H_2O$ and $CO_2$.

22. An apparatus as defined in claim 19, wherein the catalytic process is a hydrogenation process.

23. An apparatus as defined in claim 22, wherein the hydrogenation process is configured to consume $H_2$ in the extracted gas and transform at least some hydrocarbon gases in the extracted gas into other hydrocarbon gases of higher molecular weight.

24. An apparatus as defined in claim 1, wherein said optical absorption measurement system includes an optical pathway for propagating the electromagnetic energy from the one or more electromagnetic energy sources, at least part of the extracted gas lying in the optical pathway.

25. An apparatus as defined in claim 24, wherein the optical pathway is a first optical pathway, the optical absorption measurement system including a second optical pathway for propagating electromagnetic energy from the one or more electromagnetic energy sources, a reference gas lying in the second optical pathway.

26. An apparatus as defined in claim 25, wherein the first optical pathway converges with the second optical pathway subsequent to the first optical pathway traversing the extracted gas and the second optical pathway traversing the reference gas.

27. An apparatus as defined in claim 24, wherein the optical absorption signals produced by the analyser include first optical absorption signals and second optical absorption signals, said absorption measurement system being configured to:
   i) use the one or more electromagnetic energy sources to excite the extracted gas to produce the first optical absorption signals;
   ii) apply the catalytic process to the extracted gas to derive a modified extracted gas; and
   iii) use the one or more electromagnetic energy sources to excite the modified extracted gas to produce the second optical absorption signals.

28. An apparatus as defined in claim 27, wherein the one or more electromagnetic energy sources are used to excite the modified extracted gas to produce the second optical absorption signals after completion or interruption of the application of the catalytic process to the extracted gas.

29. An apparatus as defined in claim 27, wherein the one or more electromagnetic energy sources are used to excite the modified extracted gas to produce the second optical absorption signals during the application of the catalytic process to the extracted gas.

30. An apparatus as defined in claim 27, wherein the one or more electromagnetic energy sources are used to excite the modified extracted gas to produce the second optical absorption signals both:
   a) during the application of the catalytic process to the extracted gas; and
   b) after completion or interruption of the catalytic process applied to the extracted gas.

31. An apparatus as defined in claim 27, wherein the optical absorption measurement system includes a temperature regulating system having at least one of a heating element and a cooling element for controlling temperature characteristics of at least one of the extracted gas and the modified extracted gas so that the temperature characteristics of the extracted gas when the first optical absorption signals are produced are similar to the temperature characteristics of the modified extracted gas when the second optical absorption signals are produced.

32. An apparatus as defined in claim 27, wherein the optical absorption measurement system controls pressure characteristics of at least one of the extracted gas and the modified extracted gas so that the pressure characteristics of the extracted gas when the first optical absorption signals are produced are similar to the pressure characteristics of the modified extracted gas when the second optical absorption signals are produced.

33. An apparatus as defined in claim 32, wherein the optical absorption measurement system includes a pressure regulating system comprising one of more actionable valves for introducing an external gas to at least one of the extracted gas and the modified extracted gas to obtain a mixed-gas, wherein the obtained mixed-gas has a pressure approaching a target pressure.

34. An apparatus as defined in claim 32, wherein the optical absorption measurement system includes a pressure regulating system having a passive element for introducing ambient air to at least one of the extracted gas and the modified extracted gas to obtain a mixed-gas, wherein the obtained mixed-gas has a pressure approaching atmospheric pressure.

35. A method for performing dissolved gas analysis on a piece of electrical equipment having components immersed in electrical insulating liquid, the method comprising:
   a) causing electrical insulating liquid to be directed to a gas extraction system for extracting gas from the electrical insulating liquid, said gas extraction system including at least one of:
      a structure defining a gas extraction space above at least a portion of the electrical insulating liquid to extract gas from the electrical insulating liquid by diffusion; and
      a semi-permeable membrane forming a phase barrier between at least a sample of the electrical insulating liquid and a gas extraction volume, the semi-permeable membrane allowing one or more gas components in the electrical insulating liquid to permeate into the gas extraction volume while restraining permeation of one or more other components;

b) using the gas extraction system to extract gas from the electrical insulating liquid;

c) using an analyzer including an optical absorption measurement system to perform gas analysis on the extracted gas, wherein using the analyzer to perform gas analysis comprises exciting the extracted gas with one or more electromagnetic energy sources and obtaining optical absorption signals associated with the gas sample:
   1) prior to application of a catalytic process to the gas sample; and
   2) during and/or after application of the catalytic process to the gas sample;

d) processing the obtained optical absorption signals to derive information associated with dissolved gas concentrations in the electrical insulating liquid.

36. A method as defined in claim 35, wherein the derived information conveys a concentration of a specific target gas in the extracted gas.

37. A method as defined in claim 35, wherein processing the obtained optical absorption signals to derive information comprises:
   a) deriving concentrations of different component species in the extracted gas;
   b) assessing the derived concentrations of the different component species to derive diagnostic information.

38. A method as defined in claim 35, wherein the information associated with the dissolved gas concentrations in the insulating liquid derived by the processing system conveys concentrations of one or more specific gases selected from the group consisting of carbon dioxide ($CO_2$), carbon monoxide (CO), ethane ($C_2H_6$), methane ($CH_4$), ethylene ($C_2H_4$) and acetylene ($C_2H_2$).

39. A method as defined in claim 35, comprising using a plurality of optical filters for filtering the electromagnetic energy from the one or more electromagnetic energy sources, the optical filters in the plurality of optical filters being associated with respective frequency bands corresponding to specific target gases.

40. A method as defined in claim 35, comprising establishing a communication link over a computer network with a remote computing device for transmitting the derived information associated with dissolved gas concentrations in the electrical insulating liquid.

41. A method as defined in claim 35, wherein said piece of electrical equipment includes at least one of a transformer, a tap-changer and a circuit breaker.

42. A method as defined in claim 35, wherein at least one of the one or more electromagnetic energy sources is an IR electromagnetic energy source and wherein the optical absorption signals are IR absorption signals.

43. A method as defined in claim 35, wherein at least one of the one or more electromagnetic energy sources is an UV electromagnetic energy source and wherein the optical absorption signals are UV absorption signals.

44. A method as defined in claim 35, wherein the catalytic process includes heating a catalytic element to initiate or accelerate the catalytic process.

45. A method as defined in claim 35, comprising adjusting temperature and pressure characteristics of the extracted gas so that the optical absorption signals are obtained at similar temperatures and pressures.

46. A method as defined in claim 35, wherein the catalytic process includes at least one of a combustion process and a hydrogenation process.

47. A method as defined in claim 46, wherein the catalytic process includes a combustion process.

48. A method as defined in claim 47, wherein the combustion process is configured to combust at least some combustible gases in the extracted gas in a process that consumes $O_2$ and forms combustion by-products including at least one of $H_2O$ and $CO_2$.

49. A method as defined in claim 46, wherein the catalytic process is a hydrogenation process.

50. A method as defined in claim 49, wherein the hydrogenation process is configured to consume $H_2$ in the extracted gas and transform at least some hydrocarbon gases in the extracted gas into other hydrocarbon gases of higher molecular weight.

51. A method as defined in claim 35, comprising using said optical absorption measurement system for propagating the electromagnetic energy from the one or more electromagnetic energy sources over an optical pathway, at least part of the extracted gas lying in the optical pathway.

52. A method as defined in claim 51, wherein the optical absorption signals produced by the analyser include first optical absorption signals and second optical absorption signals, said method comprising:
   i) using the one or more electromagnetic energy sources to excite the extracted gas to produce the first optical absorption signals;
   ii) applying the catalytic process to the extracted gas to derive a modified extracted gas; and
   iii) using the one or more electromagnetic energy sources to excite the modified extracted gas to produce the second optical absorption signals.

53. A method as defined in claim 52, comprising controlling temperature characteristics of at least one of the extracted gas and the modified extracted gas so that the temperature characteristics of the extracted gas when the first optical absorption signals are produced are similar to the temperature characteristics of the modified extracted gas when the second optical absorption signals are produced.

54. A method as defined in claim 52, comprising controlling pressure characteristics of at least one of the extracted gas and the modified extracted gas so that the pressure characteristics of the extracted gas when the first optical absorption signals are produced are similar to the pressure characteristics of the modified extracted gas when the second optical absorption signals are produced.

55. A method as defined in claim 54, wherein controlling the pressure characteristics of at least one of the extracted gas and the modified extracted gas includes introducing an external gas to at least one of the extracted gas and the modified extracted gas to obtain a mixed-gas, wherein the obtained mixed-gas has a pressure approaching a target pressure.

56. A method as defined in claim 54, wherein controlling the pressure characteristics of at least one of the extracted gas and the modified extracted gas includes introducing ambient air to at least one of the extracted gas and the modified extracted gas to obtain a mixed-gas, wherein the obtained mixed-gas has a pressure approaching atmospheric pressure.

* * * * *